US012679876B2

(12) United States Patent  
Choe et al.

(10) Patent No.: US 12,679,876 B2  
(45) Date of Patent: Jul. 14, 2026

(54) ACTIVIN/BMP7 CHIMERAS: SUPER-ACTIVE SAB704 AND SAB715, AND THEIR RESPECTIVE NOGGINSENSITIZED VARIANTS, NAB704 AND NAB715; AND NAB204

(71) Applicant: OSR Holdings Co., Ltd., Gyeonggi-do (KR)

(72) Inventors: Seunghyon Choe, Incheon (KR); So-Mi Yoon, Incheon (KR)

(73) Assignee: OSR Holdings Co., Ltd., Gyeonggi-do (KR)

( * ) Notice: Subject to any disclaimer, the term of this patent is extended or adjusted under 35 U.S.C. 154(b) by 1051 days.

(21) Appl. No.: 17/294,497

(22) PCT Filed: Nov. 13, 2019

(86) PCT No.: PCT/KR2019/015478  
§ 371 (c)(1),  
(2) Date: May 17, 2021

(87) PCT Pub. No.: WO2020/101366  
PCT Pub. Date: May 22, 2020

(65) Prior Publication Data  
US 2021/0395322 A1      Dec. 23, 2021

Related U.S. Application Data

(60) Provisional application No. 62/767,707, filed on Nov. 15, 2018.

(51) Int. Cl.  
*C07K 14/495* (2006.01)  
*A61K 38/00* (2006.01)  
*C07K 14/51* (2006.01)

(52) U.S. Cl.  
CPC ............ *C07K 14/495* (2013.01); *C07K 14/51* (2013.01); *A61K 38/00* (2013.01)

(58) Field of Classification Search  
None  
See application file for complete search history.

(56) References Cited

U.S. PATENT DOCUMENTS 8,952,130 B2 *  2/2015  Choe ...................... A61P 21/02  
536/23.1  
2010/0221777 A1      9/2010  Choe et al.

FOREIGN PATENT DOCUMENTS

CN            101516388  A      8/2009  
WO      WO-2008-051526 A2      5/2008  
WO      WO-2017/209519 A1      12/2017

OTHER PUBLICATIONS

International Search Report from corresponding PCT Application No. PCT/KR2019/015478, dated Feb. 25, 2020.  
Allendorph, George P., et al.; "Designer TGFB superfamily ligands with diversified funcitonality", PLoS ONE, 2011, vol. 6, issue 11, e26402, p. 1*12.  
Yoon, Byung-Hak, et al.; "An activin A/BMP2 chimera, AB204, displays bone-healing properties superior to those BMP2", JBMR, 2014, vol. 29, No. 9, pp. 1950-1959.  
Kim, Meejung, et al.; "The activin-βA/BMP-2 chimera AB204 is a strong stimulator of adipogenesis", Journal of Tissue Engineering and Regenerative Medicine, 2017, vol. 11, pp. 1524-1531.  
Radhika V. Korupolu, et al, "Activin A/Bone Morphogenetic Protein (BMP] Chimeras Exhibit BMP-like Activity and Antagonize Activin and Myostatin", The Journal of Biological Chemistry, Feb. 15, 2008, pp. 3782-3790.  
Office Action from corresponding Chinese Patent Application No. 201980075594.3 issued on Dec. 11, 2023.  
Extended European Search Report from corresponding European Patent Application No. 19885240.2 issued on Dec. 21, 2021.

* cited by examiner

*Primary Examiner* — Tara L Martinez  
(74) *Attorney, Agent, or Firm* — Harness, Dickey & Pierce, P.L.C.

(57) ABSTRACT

The present disclosure relates to chimeric polypeptide having TGF-beta activity, nucleic acids encoding the polypeptides, and host cells for producing the polypeptides with improved or novel biological and therapeutic properties.

5 Claims, 14 Drawing Sheets

Specification includes a Sequence Listing.

FIG. 2

Activin A (SEQ ID NO. 1)
ATGGGCCTGGAGTGCGACGGCAAGGTCAACATCTGCTGTAAGAAACAGTTCTTTGTCAGTTTCAAGGACATCGGCTGGAATGACTGGA TCATTGCTCCCTCTGGCTATCATGCCAACTACTGCGAGGGGTGAGTGCCCGAGCCATATAGCAGGCACGTCCGGGTCCTCACTGTCCTTCC ACTCAACAGTCATCAACCACTACGCATGCCGGCCATAGCCCCTTTGCCAACCTCAAATCGTGCTGTGTGCCCACCAAGCTGAGACCCATG TCCATGTTGTACTATGATGATGGTCAAAACATCATCAAAAAGGACATTCAGAACATGATCGTGGAGGAGTGCGGGTGCTCC BMP2 (SEQ ID NO. 2)
ATGCAAGCCAAACACAAACAGCGGAAGCGTCTTAAGTCCAGCTGCAAAAGGCACCCTTTGTATGTGGACTTCAGTG
ATGTGGGGGTGGAATGACTGGATCATTGCTCCCTCTGGCTATCATGCCAACTACTGCGACGGAGAATGCCCTTTTCCT
CTGGCTGA
TCATCTGAACTCCACTAATCATGCCATTGTTCAGACGTTGGTCAACTCTGTTAACTCTAAGATTCCTAAGGCATGCTG
TGTCCCGACCAAGCTGAGACCCATGTCCATGTTGTACTATGATGATGGTCAAAACATCATCAAAAAGGACATTCAGA
ACATGATCGTGGAGGAGTGTGGGTGCTCA 1B3-BMP-7 (SEQ ID NO. 3)
ATGCAAGCCAAACACAAACAGCGGAAACGCCCTTAAGTCCAGCTGTAAGAGACACCCCTTTGTACGTGGACTTCAGTG
ACGTGGGGGTGGAATGACTGGATTATCGCGCCTGAAGGCTACCGCCGCCTACTACTGTGAGGGGGAGTGTGCCTTCC
CTCTGAACTCCTACATGAACGCCACCAACCACGCCATCGTGCAGACGCTGGTCCACTTCATCAACCCCGGAAACGGT
GCCCAAGCCCTGCTGTGTGCGCCCACGCAGCTCAATGCCATCTCCGTCCTCTACTTCGATGACAGCTCCAACGTCATC
CTGAAGAAATACAGAAACATGGTGGTCCGGGCCTGTGGCTGCCAC Activin A (SEQ ID NO. 4)
MGLECDGKVNICCKKQFFVSFKDIGWND - WIIAPSGYHANYCEGECP - SHIAGTSGSSLSFHSTVIN -
HYRMRGHSPFANLKSCCVP - TKLRPMSMLYYD - DGQNIIKKDIQNMIVEECGCS BMP2 (SEQ ID NO. 5)
MQAKHKQRKRLKSSCKRHPLYVDFSDVGWND - WIIAPPGYHAFYCHGECP - FPLADHLNSTNHAIVQTLVN -
SVNSKIPKACCVP - TELSAISMLYLD - ENEKVVLKNYQDMVVEGCGCR BMP7 (SEQ ID NO. 6)
MSTGSKQRSQNRSKTPKNQEALRMANVAENSSSDQRQACKKHELYVSFRDLGWQD - WIIAPEGYAAYYCEGECA -
FPLNSYMNATNHAIVQTLVH - FINPETVPKPCCAP - TQLNAISVLYFD - DSSNVILKKYRNMVVRACGCH AB204 (SEQ ID NO. 7)
MQAKHKQRKRLKSSCKRHPLYVDFSDVGWND - WIIAPSGYHANYCDGECP - FPLADHLNSTNHAIVQTLVN -
SVNSKIPKACCVP - TKLRPMSMLYYD - DGQNIIKKDIQNMIVEECGCS NAB204 (SEQ ID NO. 8)
MQAKHKQRKRLKSSCKRHPLYVDFSDVGWND - WIIAPSGYHANYCDGECP - FPLADHLNSTNHAIVQTLVN -
SVNSKIPKACCVP - TKLRPMSMLYYD - DGQNVILKKYQNMIVEECGCS SAB704 (SEQ ID NO. 9)
MSTGSKQRSQNRSKTPKNQEALRMANVAENSSSDQRQACKKHELYVSFRDLGWQD - WIIAPSGYHANYCEGECP -
FPLNSYMNATN - HAIVQTLVHFINPETVPKPCCAP - TKLRPMSMLYYD - DGQNIIKKDIQNMIVEECGCS NAB704 (SEQ ID NO. 10)
MSTGSKQRSQNRSKTPKNQEALRMANVAENSSSDQRQACKKHELYVSFRDLGWQD - WIIAPSGYHANYCEGECP -
FPLNSYMNATN - HAIVQTLVHFINPETVPKPCCAP - TKLRPMSMLYYD - DGQNVILKKYQNMIVEECGCS SAB715 (SEQ ID NO. 11)
MSTGSKQRSQNRSKTPKNQEALRMANVAENSSSDQRQACKKHELYVSFRDLGWQD - WIIAPSGYHANYCEGECP -
FPLNSYMNATN - HAIVQTLVHFINPETVPKPCCAP - TQLNAISVLYFD - DGQNIIKKDIQNMIVEECGCS NAB715 (SEQ ID NO. 12)
MSTGSKQRSQNRSKTPKNQEALRMANVAENSSSDQRQACKKHELYVSFRDLGWQD - WIIAPSGYHANYCEGECP -
FPLNSYMNATN - HAIVQTLVHFINPETVPKPCCAP - TQLNAISVLYFD - DGQNVILKKYQNMIVEECGCS 1B2BMP7 (SEQ ID NO. 13)
MQAKHKQRKRLKSSCKRHPLYVDFSDVGWND WIIAPEGYAAYYCEGECA FPLNSYMNATNHAIVQTLVH
FINPETVPKPCCAP - TQLNAISVLYFD - DSSNVILKKYRNMVVRACGCH Luciferase assay:
SAB704/ C2C12 cells/ with ID1-luc, SMAD1

BMP7 (pepro) EC50: 423.1ng/ml
SAB704 EC50: 15.57ng/ml
SAB715 EC50: 235.1ng/ml

ACAN

SOX9

ADAMTS-5

FIG. 5

ACTIVIN/BMP7 CHIMERAS: SUPER-ACTIVE SAB704 AND SAB715, AND THEIR RESPECTIVE NOGGINSENSITIZED VARIANTS, NAB704 AND NAB715; AND NAB204

CROSS-REFERENCE TO RELATED APPLICATIONS

This application is a national phase application of PCT Application No. PCT/KR2019/015478 filed on 13 Nov. 2019, which claims the benefit of and priority to U.S. Patent Application No. 62/767,707 filed on 15 Nov. 2018. The entire disclosures of the applications identified in this paragraph are incorporated herein by references.

TECHNICAL FIELD

The present disclosure relates to biomolecular engineering and design, and engineered proteins and nucleic acids.

BACKGROUND ART

Activins and Bone Morphogenetic Proteins (BMPs) are members of the much larger Transforming Growth Factor-beta (TGF-beta) superfamily. Given their pervasiveness in numerous developmental and cellular processes, TGF-beta ligands are candidates to be engineered for therapeutic purposes. The ability to specifically modify, enhance, and alter such biological properties by the engineered TGF-beta ligands are the discovery basis of this disclosure.

DISCLOSURE OF INVENTION

Solution to Problem

In accordance with an aspect of the present disclosure, there is provided a recombinant polypeptide comprising and containing: at least two peptide segments each derived from two different polypeptides, a first segment of the polypeptide comprising a sequence having at least 90% identity from a first TGF-beta family protein and the second peptide segment comprising a sequence having at least 90% identity to a second TGF-beta family protein, wherein the segments are operably linked and have activity of at least two of the first or second parental TGF-beta family protein, or activity of new in vivo signaling and cellular properties, wherein at least two polypeptide segments comprise 6 peptide segments operably linked N- to C-terminal and wherein the polypeptide modulates the SMAD pathway.

In one embodiment, the disclosure provides a recombinant polypeptide comprising of six segments in total: at least two peptide segments comprising a sequence having at least 90% identity from a first TGF-beta family parental protein, and the other peptide segments comprising a sequence having at least 90% identity to a second TGF-beta family parental protein, wherein these six segments collectively are operably linked in the order of Segments 1, 2, 3, 4, 5, 6, and the resulting polypeptide chimeras have enhanced activity of at least one or both of two parental TGF-beta family proteins.

In one embodiment, the polypeptide comprises an N-terminal Segment 1 from BMP-2, wherein at least two polypeptide segments comprise 6 peptide segments operably linked N- to C-terminal.

In one embodiment, the first TGF-beta family protein is BMP-2 and the second TGF-beta family protein is Activin or other family member, wherein each segment corresponds to a structural motif of the common Segment of the two and wherein the polypeptide modulates the SMAD pathway.

In one embodiment, the polypeptide comprises an N-terminal Segment 1 from BMP-7, wherein at least two polypeptide segments comprise 6 peptide segments operably linked N- to C-terminus.

In one embodiment, the first TGF-beta family protein is BMP-7 and the second TGF-beta family protein is Activin or other family member, wherein each Segment corresponds to a structural motif of the common Segment of the two and and wherein the polypeptide modulates the SMAD pathway.

In one embodiment, the Segments 1, 3, and 4 of BMP7 and Segments 2, 5, and 6 of Activin are operably linked to generate SAB704 and wherein the polypeptide modulates the SMAD pathway.

In one embodiment, the Segments 1, 3, 4, and 5 of BMP7 and Segments 2 and 6 of Activin are operably linked to generate SAB715 and wherein the polypeptide modulates the SMAD pathway.

In a more preferred embodiment, the invention provides design-augmented (DA) TGF-beta ligands that can be synthesized by selecting and conjoining different sequence segments of TGF-beta superfamily ligands to construct new ligands ("DA chimeras"). These novel ligands possess entirely new protein sequence library that differ from their naturally existing parental ligands. This approach originates primarily from the recognition of the structural commonality among natural TGF-beta superfamily ligands. All ~40 TGF-beta superfamily ligands share the same overall architecture with generic characteristics for each region of the protein. The framework of TGF-beta ligands can be divided into (generally) six subdomains (also called sequence Segments; marked in six different colors in FIG. 1) that all superfamily members share.

The disclosure also provides a design principle for a chimeric TGF-beta family polypeptide comprising a segment of a first TGF-beta family protein, for instance, protein noted as "A", operably linked to a segment of a second different TGF-beta family protein, for instance, protein noted as "B", wherein the polypeptide chimeras have an order of Segment 1-Segment 2-Segment 3-Segment 4-Segment 5-Segment 6, for which each Segment of the chimera is derived from the Segment of the corresponding number of either A or B, resulting in different DA chimeras as described in the present disclosure, to provide different SMAD-modulating activity (Gray & Choe, 2019, "Design-augmented (DA) biologics: BMP Chimeras for bone and cartilage regeneration, Osteoarthritis and Cartilage, in press, DOI: doi.org/10.1016/j.joca.2019.09.004).

The sequence boundaries of these chimeras are derived from the claims priority made in U.S. Provisional Application Ser. No. 61/155,066, filed, Feb. 24, 2009, in which Activin and Bone Morphogenetic Protein 2 (referred to as BMP-2) chimeras, including AB204 and AB215, have been claimed to produce the super-active signaling ability compared to their parental proteins, Activin and BMP-2 (as referred to in FIG. 2).

In accordance with another aspect of the present disclosure, there is provided a chimeric TGF-beta family polypeptide comprising a segment of a first TGF-beta family protein operably linked to a segment of a second different TGF-beta family protein to provide a chimeric polypeptide having SMAD-modulating activity, wherein each segment corresponds to a structural motif of the common Segment of the two.

In accordance with another aspect of the present disclosure, there is provided a sequence variant of the polypeptide of claim 1, wherein 6 amino acids-long Noggin-sensitizer sequence replaces the structurally-equivalent region of the said polypeptide to generate NAB204 (from AB204), NAB704 (from SAB704), or NAB715 (from SAB715) to modulate their Noggin-binding capability, respectively.

In accordance with another aspect of the present disclosure, there is provided a sequence variant of the polypeptide of TGF-beta superfamily wherein Noggin-sensitive- (NS-) sequence can be introduced using the 6 amino acids-long Noggin-sensitizer sequence derived from its related subfamily sequence to generate Noggin-sensitive form such as NS-Activin (from Activin) as one such chimera example, or be removed from it by replacing the same 6 amino-acids-long Noggin-sensitizer sequence with its Noggin-insensitive- (NIS-) sequence derived from its related subfamily sequence to generate NIS-BMP2 (from BMP2) as one such chimera example.

This disclosure provides specifically three non-naturally occurring chimeras, each comprises of six peptide Segments having their protein sequences derived from their parental proteins, Activin and Bone Morphogenetic Protein 7 (referred to as BMP-7, SEQ ID NO: 6, FIG. 2). Two chimeras, named as SAB704 and SAB715, operably linked from the N-terminus to the C-terminus in the order of Segments 1, 2, 3, 4, 5, 6 for the purpose of modulating a SMAD pathway naturally associated with Activin and BMP-7 (SEQ ID NOs: 9 and 11, respectively, FIG. 2).

The other two chimeras, named as NAB704 and NAB715 (SEQ ID NOs: 10 and 12, respectively, FIG. 2), are a sequence variant of SAB704 and SAB715, respectively, for which five or less than five amino acid residues have been changed in the sequence of Segment 6 of SAB704 and SAB715, respectively. As a result, NAB704 and NAB715 are Noggin-sensitive that is defined to be able to physically bind to and be responsive to the presence of Noggin in vivo, by design specifically for their biological functions, whereas SAB704 and SAB715 are Noggin-insensitive and super-active in their cellular signaling ability by design. Additionally, this disclosure also identifies the sequence of the third DA chimera that is Noggin-sensitive, NAB204 (SEQ ID NO: 8 in FIG. 2) as a comparable variant of AB204 (SEQ ID NO: 7 in FIG. 2) derived from the invention related to US Provisional filing No. 61/155,066.

Design Basis of SAB704, SAB715, NAB204, NAB704, and NAB715

In one embodiment, the polypeptide chimera, SAB704, comprises 3 segments, Segments 2, 5, and 6 derived from Activin A ("A"), and 3 segments, Segments 1, 3, and 4 derived from BMP-7 ("B"), wherein these segments are operably linked from N-terminus to C-terminus in the order of Segments 1, 2, 3, 4, 5, and 6, as termed as "1B2A3B4B5A6A". The sequence boundaries of SAB704 are derived from the claims priority made in U.S. Provisional Application Ser. No. 61/155,066, filed, Feb. 24, 2009 (FIG. 5).

In yet a further embodiment, the polypeptide chimera, SAB715, comprises 2 segments, Segments 2, and 6 derived from Activin A ("A"), and 4 segments, Segments 1, 3, 4, and 5 derived from BMP-7 ("B"), wherein these segments are operably linked from N-terminus to C-terminus in the order of Segments 1, 2, 3, 4, 5, and 6, as termed as "1B2A3B4B5B6A". The sequence boundaries of SAB715 are derived from the claims priority made in U.S. Provisional Application Ser. No. 61/155,066, filed, Feb. 24, 2009.

In yet a further embodiment, the polypeptide chimera, NAB204, has five new amino acids that replace a six-residues part within Segment 6 of AB204, from IIKKDI (SEQ ID NO: 43) to VVLKKY (SEQ ID NO: 44). IIKKDI (SEQ ID NO: 43) is originally derived from Activin A (underlined in SEQ ID NO: 4, FIG. 2), whereas VVLKKY (SEQ ID NO: 44) is originally derived from BMP2 (underlined in SEQ ID NO: 5, FIG. 2). This six-residues part within Segment 6 is herein defined as "Noggin-sensitizer", and its protein sequence is similar among all Noggin-binding BMPs, including BMP-2 and BMP-7 (VILKKY (SEQ ID NO: 45) in BMP7, underlined in SEQ ID NO: 7, FIG. 2). These amino acid changes introduced into AB204 alter the biological property of AB204, resulting in NAB204 (SEQ ID NO: 8, FIG. 2) becoming capable of binding to Noggin (FIG. 4*b*) so that it becomes functionally sensitive to the antagonistic action of Noggin in vivo, defined herein as being "Noggin-sensitized". The protein sequence of AB204 is derived from the claims priority made in U.S. Provisional Application Ser. No. 61/155,066, filed, Feb. 24, 2009.

In yet a further embodiment, the polypeptide chimera, NAB704, has four new amino acids that replace the Noggin-sensitizer sequence of SAB704, from IIKKDI (SEQ ID NO: 43) to VILKKY (SEQ ID NO: 45). These amino acid changes alter the biological property of SAB704, resulting in NAB704 becoming capable of binding to Noggin so that it becomes functionally sensitive to the antagonistic action of Noggin in vivo (FIG. 4*a*).

In yet a further embodiment, the polypeptide chimera, NAB715, has four new amino acids that replace the Noggin-sensitizer sequence of SAB715, from IIKKDI (SEQ ID NO: 43) to VILKKY (SEQ ID NO: 45). These amino acid changes alter the biological property of SAB715, resulting in NAB715 becoming capable of binding to Noggin so that it becomes functionally sensitive to the antagonistic action of Noggin in vivo. (FIG. 4*a*).

Because of the sequence similarities, the Noggin-sensitizer sequences can comprise of replacement of five or less than five amino acids identical or conservatively similar to either VVLKKY (SEQ ID NO: 44) of BMP-2 or VILKKY (SEQ ID NO: 45) of BMP-7 within the Noggin-sensitizer sequence of Activin/BMP chimeras to switch them to Noggin-sensitive or Noggin-insensitive.

In accordance with another aspect of the present disclosure, there is provided a polynucleotide encoding the polypeptide.

The disclosure also provides a polynucleotide encoding a polypeptide of the disclosure. In this embodiment, however, the present invention provides the same polypeptide sequences that have at least 90%, 95%, 98%, 99% or more identity to a sequence consisting of the segmental assembly of Activin/BMP chimeras with or without Noggin-sensitizer.

In one embodiment, the polynucleotide comprises sequences from a plurality of TGF-beta family polynucleotides operably linked to encode a functional chimeric polypeptide having SMAD-modulating activity, including bone and cartilage regeneration by combinatorial time-dependent mix of these ligands to modulate their in vivo cellular activities.

In accordance with another aspect of the present disclosure, there is provided a vector comprising the polynucleotide.

In accordance with another aspect of the present disclosure, there is provided a host cell comprising the vector.

In accordance with another aspect of the present disclosure, there is provided a host cell comprising the polynucleotide.

In accordance with another aspect of the present disclosure, there is provided A method of producing a chimeric TGF-beta polypeptide by:

(a) aligning the sequences of at least two TGF-beta family member proteins;

(b) identifying six structurally related Segments of the two family proteins;

(c) identifying points of cross-over of the two TGF-beta proteins comprising Segments at either end of the structurally related with over 90% sequence identity over at least 5 consecutive amino acids; and (d) generating a chimeric TGF-beta polypeptide comprising and containing at least Segment 1 from BMP2 to the second TGF-beta family member protein wherein the Segments are sequentially linked at the points of cross-over to generate 1B2-BMP7 as one such chimera example.

In accordance with another aspect of the present disclosure, there is provided a chimeric polypeptide produced from the method.

In accordance with another aspect of the present disclosure, there is provided a method of modulating cell proliferation or activity associated with the SMAD pathway comprising contacting a cell with the chimeric polypeptide.

In accordance with another aspect of the present disclosure, there is provided a method of treating a disease or disorder associated with bone, cartilage, neurological tissue, cardiac tissue, skeletal muscle or endocrine tissue comprising contacting the tissue with the chimeric polypeptide.

In accordance with another aspect of the present disclosure, there is provided a method of treating a cell proliferative disease or disorder comprising contacting a cell having the cell proliferative disease or disorder with the chimeric polypeptide.

In accordance with another aspect of the present disclosure, there is provided a pharmaceutical composition for preventing or treating a disease associated with bone, cartilage, neurological tissue, cardiac tissue, skeletal muscle or endocrine tissue comprising the polypeptide.

In accordance with another aspect of the present disclosure, there is provided a pharmaceutical composition for preventing or treating a cell proliferative disease comprising the polypeptide.

In a further embodiment, the present invention provides a further ground for novel ligands for other members of the TGF-beta superfamily under some claims priority of 35 U.S.C. § 119 to U.S. Provisional Application Ser. No. 61/155,066, filed, Feb. 24, 2009, entitled as "Designer Ligands of TGG-beta Superfamily Ligands", wherein the ligand is a chimeric protein with the same sequential arrangements of six Segments from a different member of the TGF-beta superfamily.

BRIEF DESCRIPTION OF DRAWINGS

FIG. 2 depicts a structure/sequence alignment of the sequences of several members of the TGF-beta superfamily and various chimeras described in this disclosure. SEQ ID NOs: 1, 2, and 3 are nucleotide sequences that have been synthetically designed for bacterial expression of Activin A, BMP2, and 1B2-BMP7 of this study disclosure, respectively. 1B2-BMP7 is the sequence that specifies a chimera of Segment 1 from BMP2 combined with Segments 2 through 6 from BMP7. This chimera is readily expressed in bacteria, and is functionally equal to BMP7. By its nature, these nucleotide sequences can vary without changing the resulting amino acid sequences described in SEQ ID NO: 4 through SEQ ID NO: 13.

Figure 1:
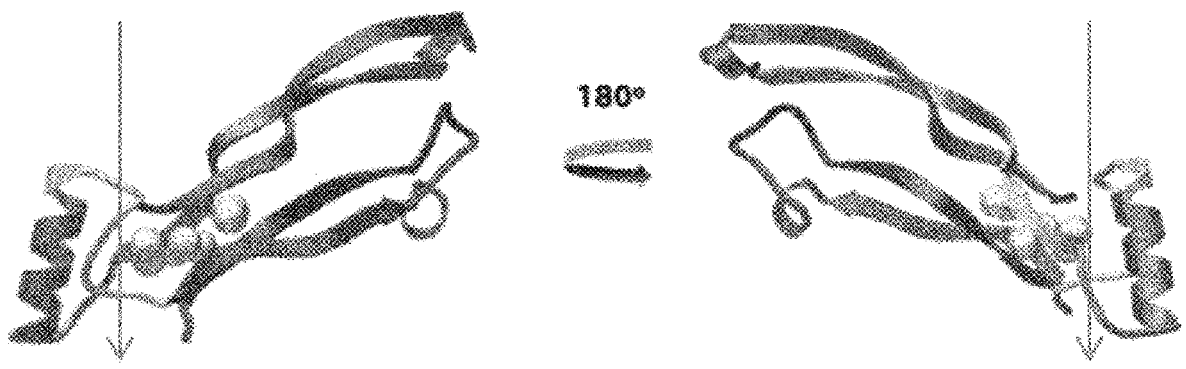
FIG. 1 shows the six Segments of a single subunit of the TGF-beta superfamily ligand's scaffold in standard ribbon diagram. A single TGF-beta superfamily ligand consists of two such subunit covalently linked together. Two subunits are related by a two-fold rotational symmetry which is vertical in this view (light-blue arrows), thus Left- and Right-panels show opposite sides of the subunit in relation to the common rotational symmetry axis. Six Segments are color-coded in RED (Segment 1), BLUE (Segment 2), YELLOW (Segment 3), GREEN (Segment 4), BROWN (Segment 5), and PURPLE (Segment 6) in the order from N-terminus to C-terminus.

SEQ ID NOs: 4, 5, and 6 are amino acid sequences of the mature region of human Activin A (colored in BLACK), human BMP2 (colored in RED), and human BMP7 (colored in BLUE) used for bacterial expression. For the reason, the sequences of these three parental molecules all begin with Methionine as the first amino acid. All relevant Segments of these chimeras are color-coded to denote their original sources in RED, BLUE, and BLACK. All six Segments are graphically separated by "-" between them for the illustration purpose only. Sequences ID No. 7 and 8 are amino acid sequences of DA chimeras, AB204 and NAB204. NAB204 contains six amino acids-long Noggin sensitizer derived from BMP2 (underlined and in RED). Sequences ID No. 9 and 10 are amino acid sequences of DA chimeras, SAB704 and NAB704. NAB704 contains six amino acids-long Noggin sensitizer derived from BMP7 (underlined and in BLUE). Sequences ID No. 11 and 12 are amino acid sequences of DA chimeras, SAB715 and NAB715. NAB715 contains six amino acids-long Noggin sensitizer derived from BMP7 (underlined and in BLUE). Sequences ID No. 13 is amino acid sequence of DA chimera, 1B2-BMP7. 1B2-BMP7 contains Segment 1 from BMP2 (in RED) and Segments 2 through 6 from BMP7 (in BLUE). 1B2-BMP7 is a substitute for BMP7 for the purpose of bacterial expression and refolding.

FIG. 3(*a*) provides cell signaling activity of the DA chimeras, SAB704, SAB715, and their parental molecule, BMP-7, as a comparison molecule (a). FIG. 3*a* illustrates that SAB704, in particular, shows approximately 30-fold increased signaling activity in C2C12 cells by SMAD1-mediated signaling pathway (Allendorph et al., Designer TGF-beta Superfamily Ligands with Diversified Functionality, PLOS One, https://doi.org/10.1371/journal-.pone.0026402, (2011)).

FIG. 3(*b*) illustrates the relative levels of RNA induction of four anabolic gene (ACAN, Aggrecan) that are known to be associated with chondrogenesis and cartilage regeneration. The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

FIG. 3(*c*) illustrates the relative levels of RNA induction of four anabolic gene (COL2A1, Collagen 2A1) that are known to be associated with chondrogenesis and cartilage regeneration. The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

FIG. 3(*d*) illustrates the relative levels of RNA induction of four anabolic gene (SOX9) that are known to be associated with chondrogenesis and cartilage regeneration. The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 3A:
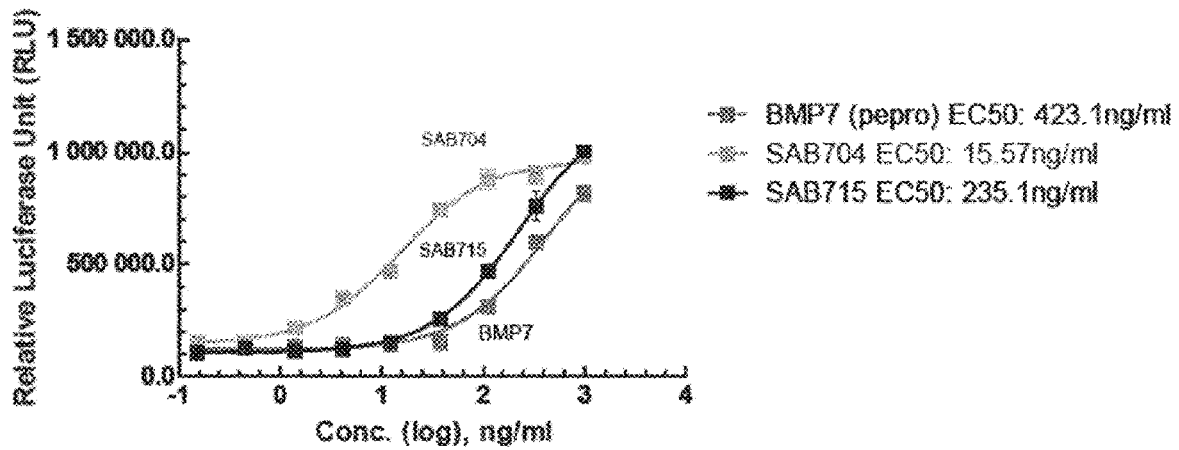
Figure 3B:
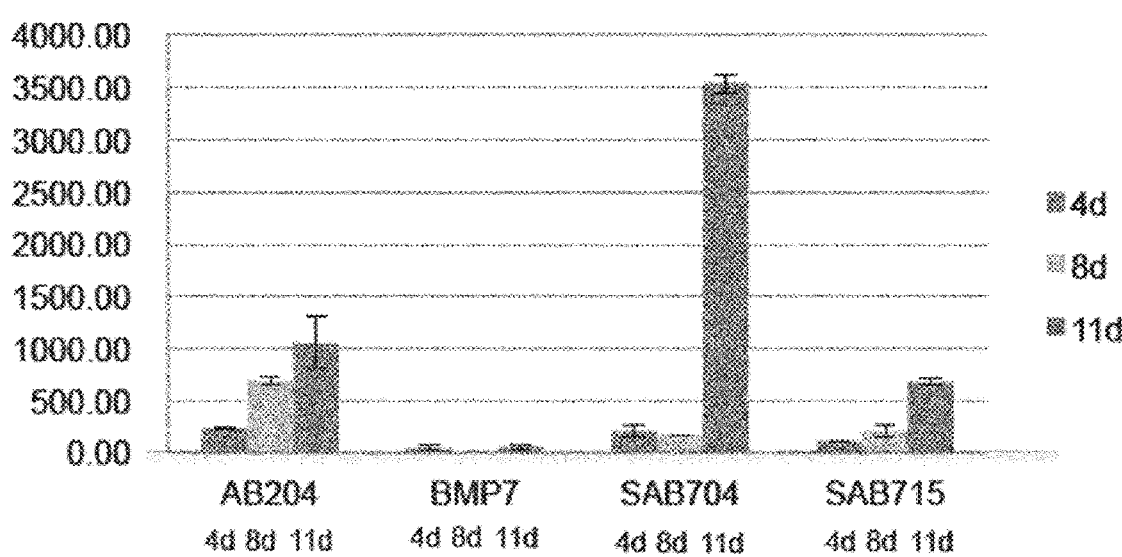
Figure 3C:
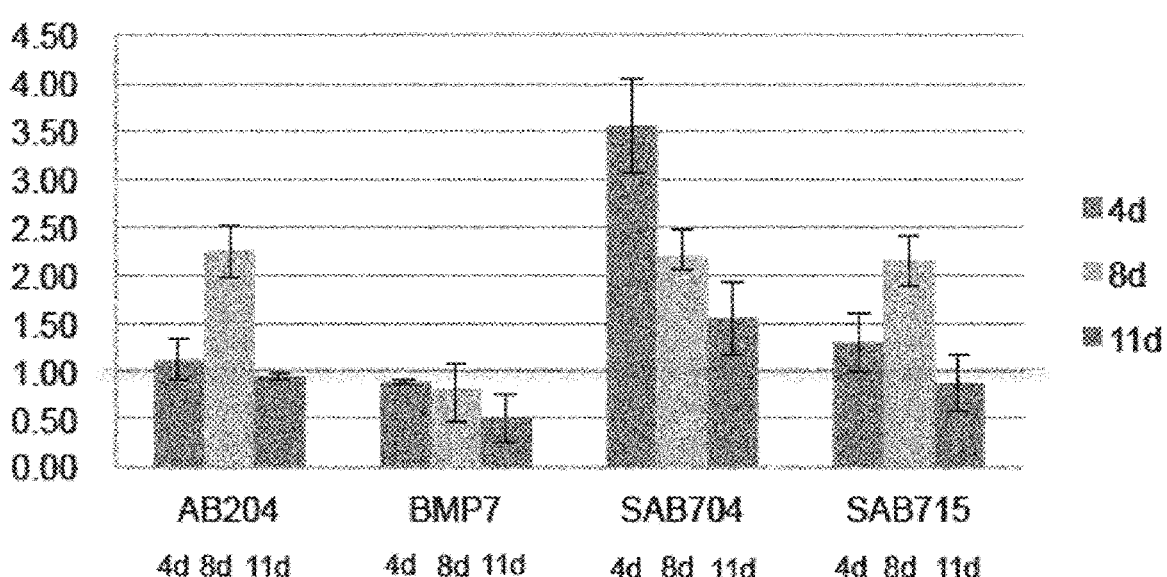
Figure 3D:
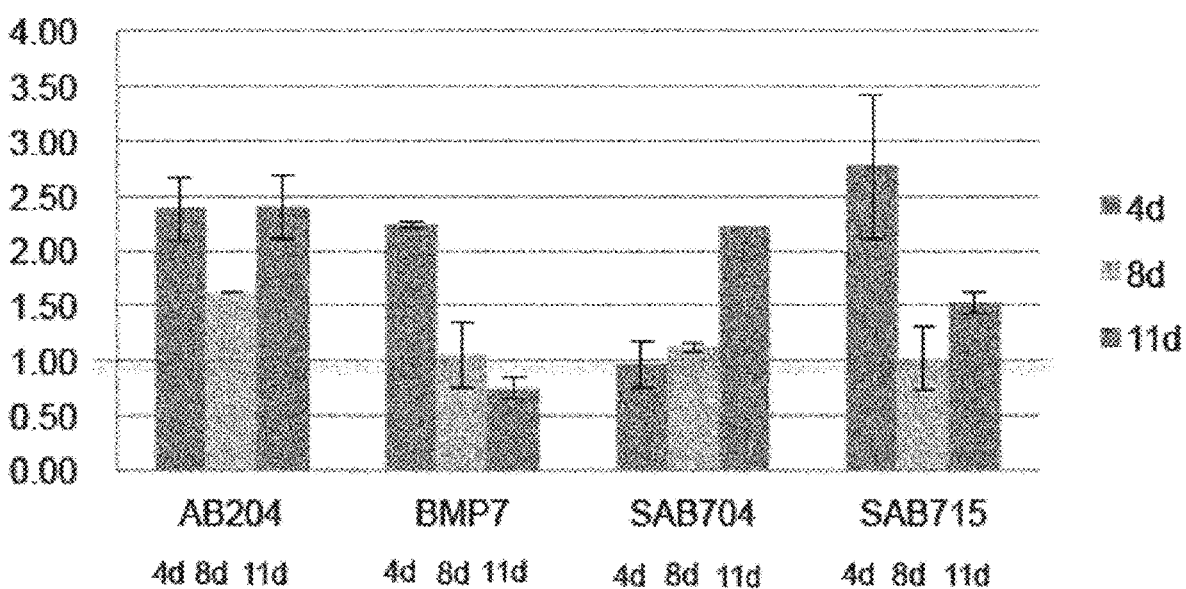
Figure 3E:
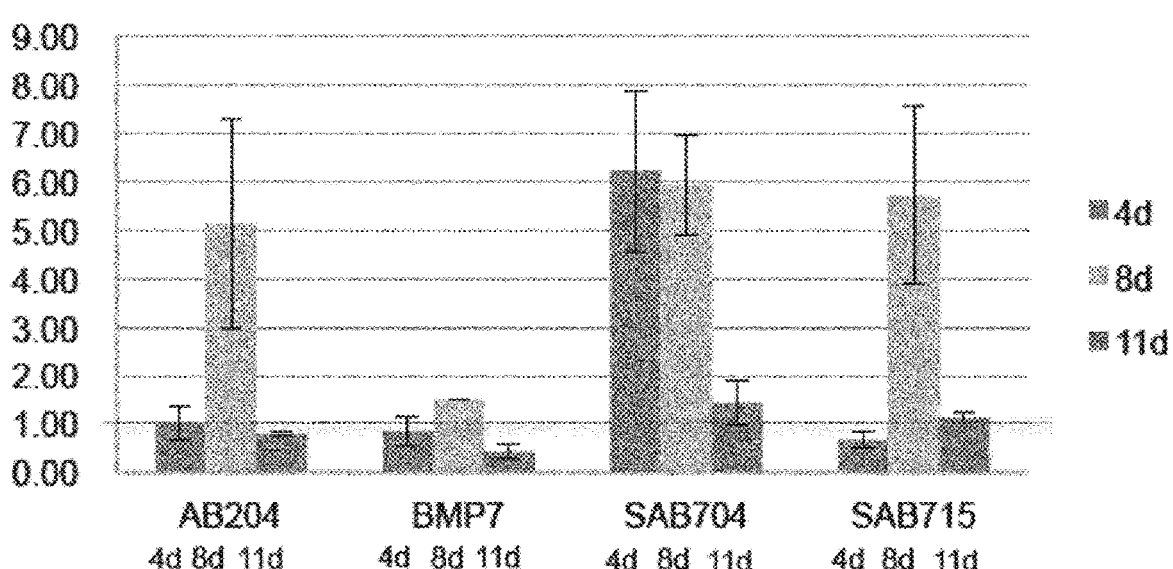

FIG. 3(e) illustrates the relative levels of RNA induction of four anabolic genes (SOX6) that are known to be associated with chondrogenesis and cartilage regeneration. The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 3F:
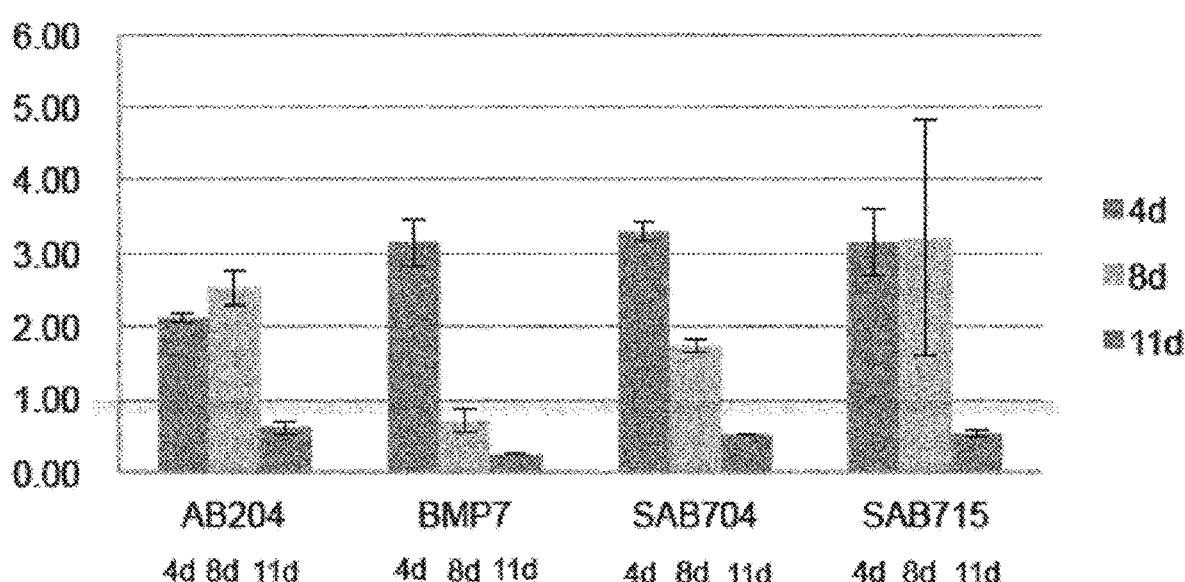

FIG. 3(f) illustrates the relative levels of RNA induction of four hypertrophic gene (MMP-13). The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 3G:
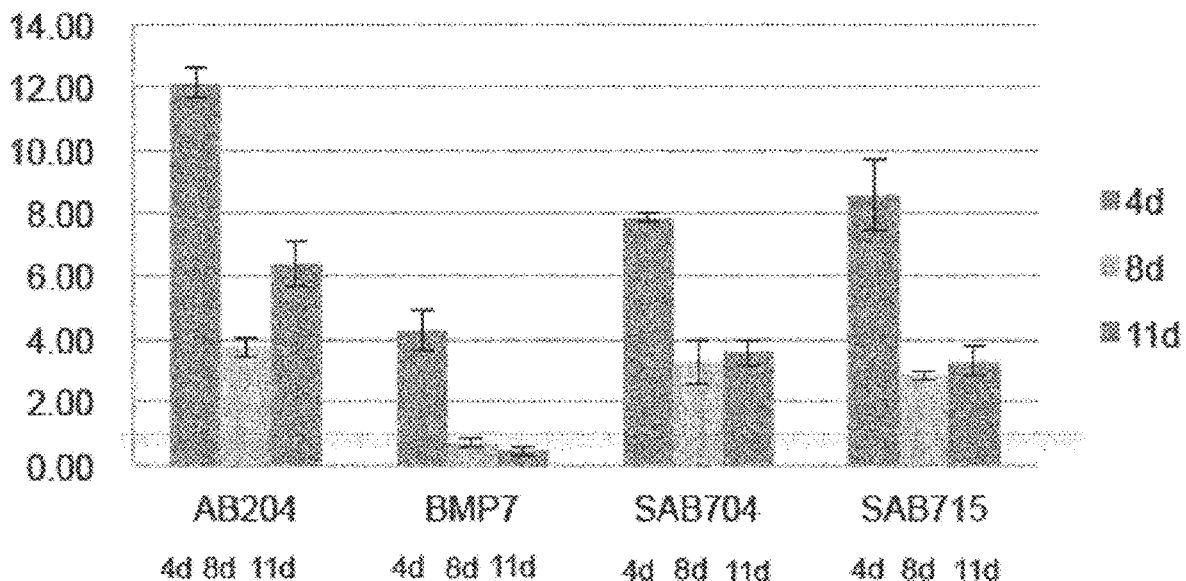

FIG. 3(g) illustrates the relative levels of RNA induction of four hypertrophic gene (ADAMTS5). The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 3H:
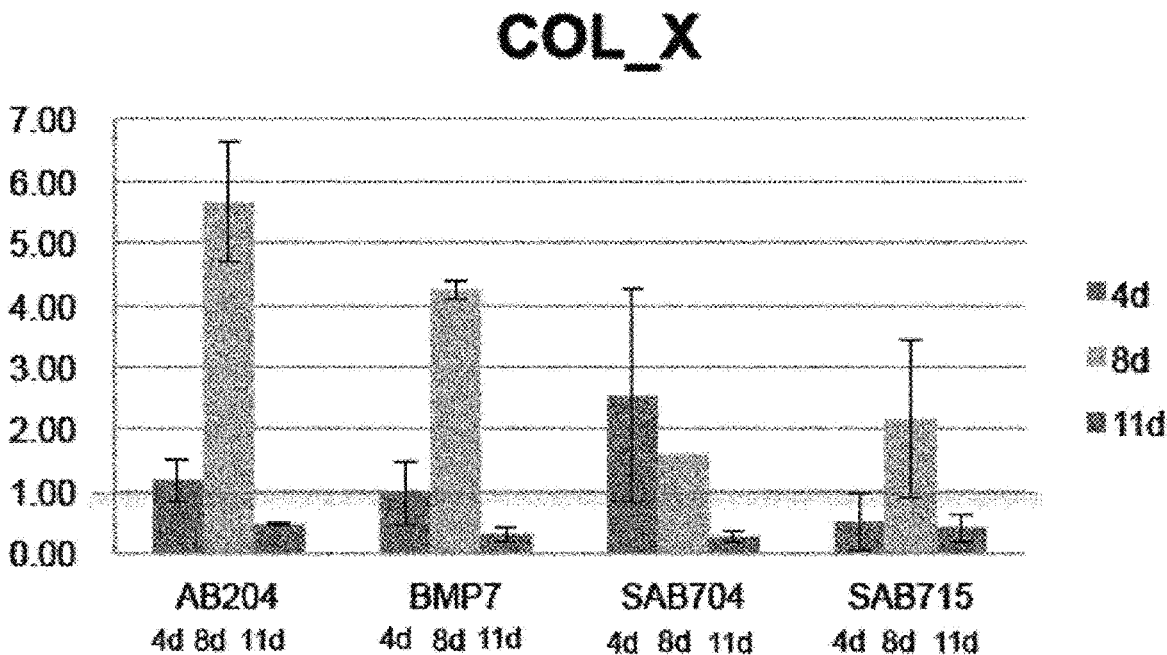

FIG. 3(h) illustrates the relative levels of RNA induction of four hypertrophic gene (COLX, Collagen X). The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 3I:
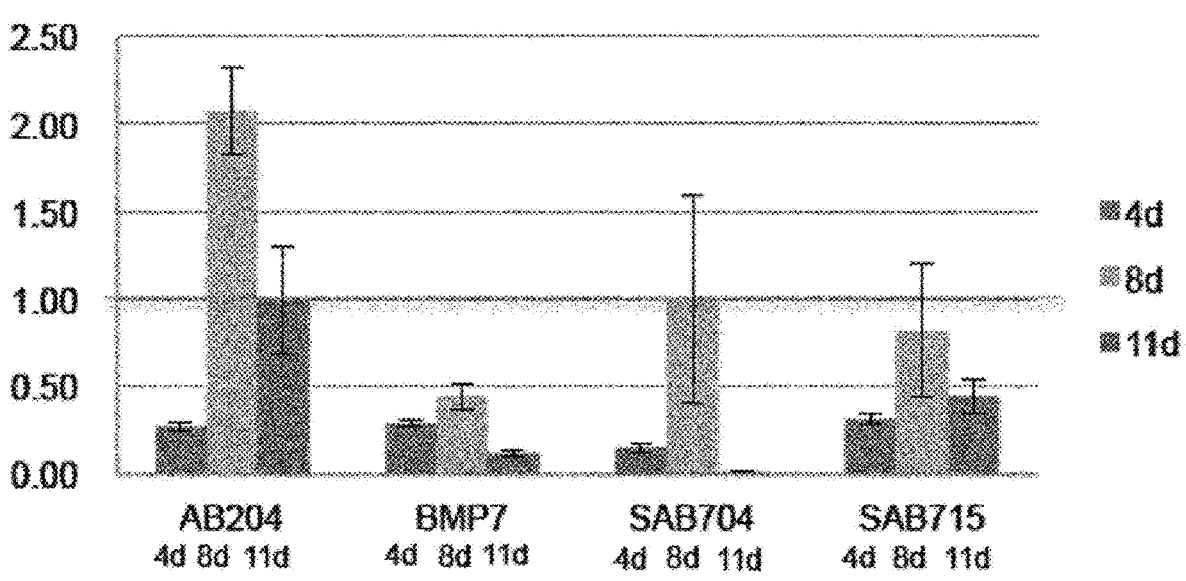

FIG. 3(i) illustrates the relative levels of RNA induction of four hypertrophic genes (RUNX2). The background level of RNA expression for each panel is noted as a horizontal line in RED as normalized at 1. After the treatments are made by these DA chimeras and BMP7, Smad-1 luciferase signaling activity is measured by the same assay methods at three time points, 4 days, 8, and 11 days.

Figure 4A:
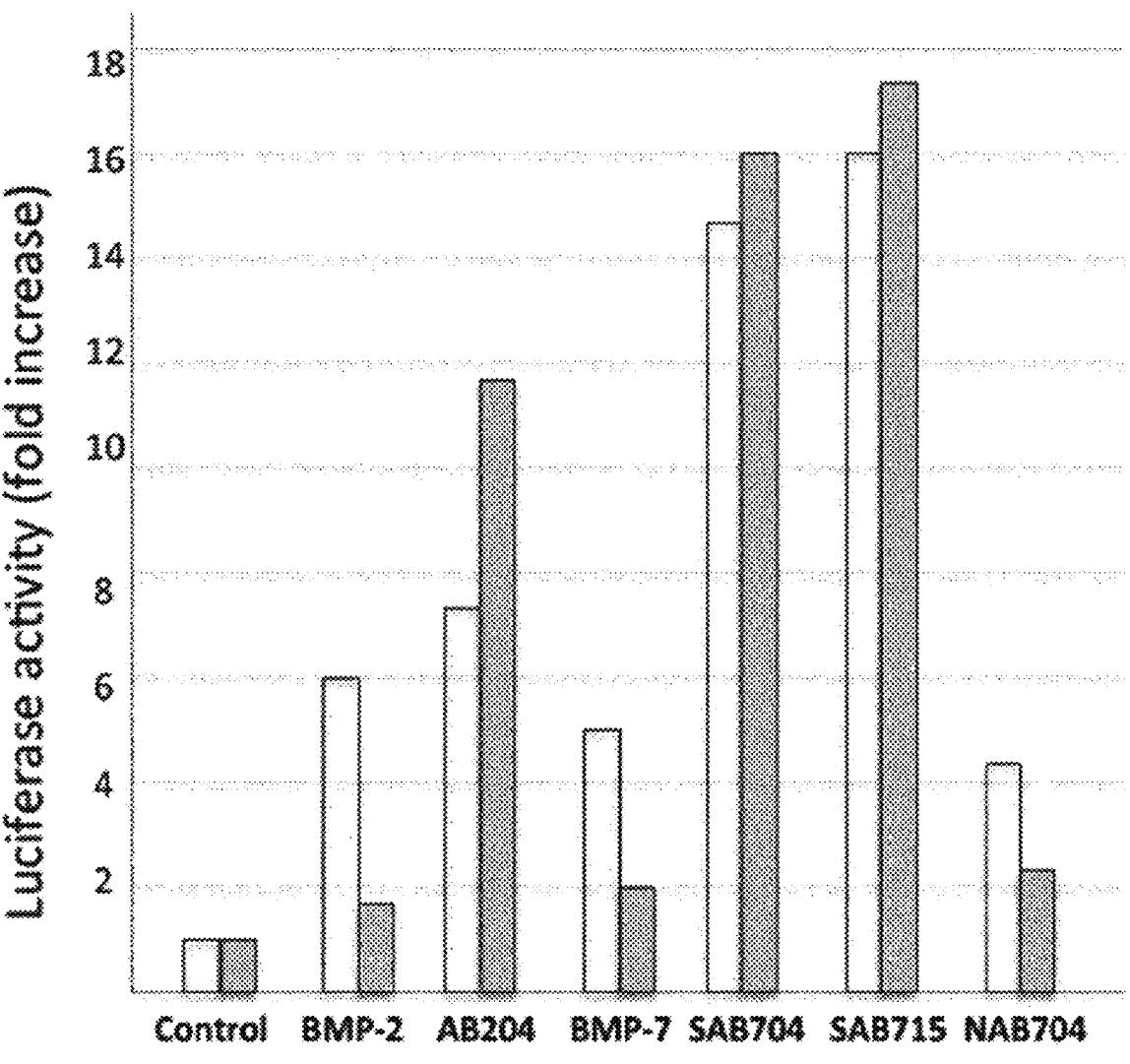

FIG. 4(a) shows Noggin sensitivity of BMP2, BMP7, and DA chimeras, AB204 and that are compared for each ligand in the absence or presence of Noggin. Smad-1 luciferase signaling activity is measured without (no shade) and with (dark shade) of Noggin treated at the equal (1:1) molar ratio between them.

Figure 4B:
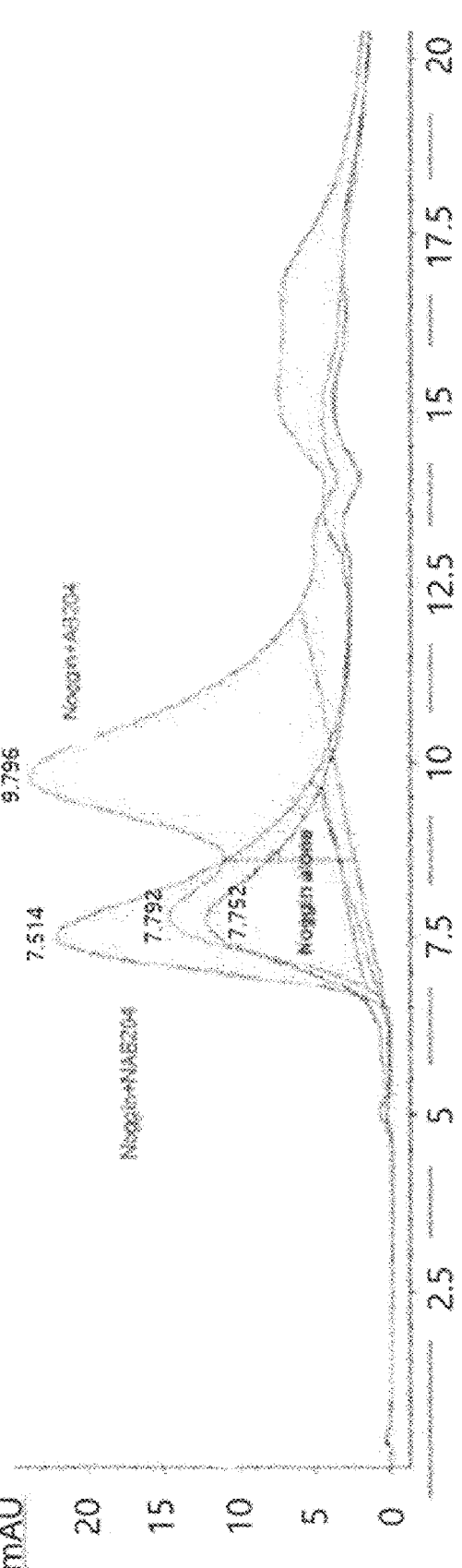

FIG. 4(b) shows the physical binding between the Noggin-sensitized chimera NAB204 in the presence of Noggin (in RED), compared to the mixture of Noggin-insensitive chimera AB204 in the presence of Noggin (in GREEN) showing no physical binding between the two molecules. This is reflected in the right-shift of the elution time of the Noggin-NAB204 complex by a size-exclusion chromatography analysis. Noggin alone is shown as a reference (in BLUE), eluting slightly slower than NAB204-Noggin complex. As a result, the Noggin binding of NAB204, NAB714, and NAB715 results in endowing them with reduced signaling activity in the presence of Noggin as for BMP2 v.s. AB204 (FIG. 4(a)).

Figure 5:
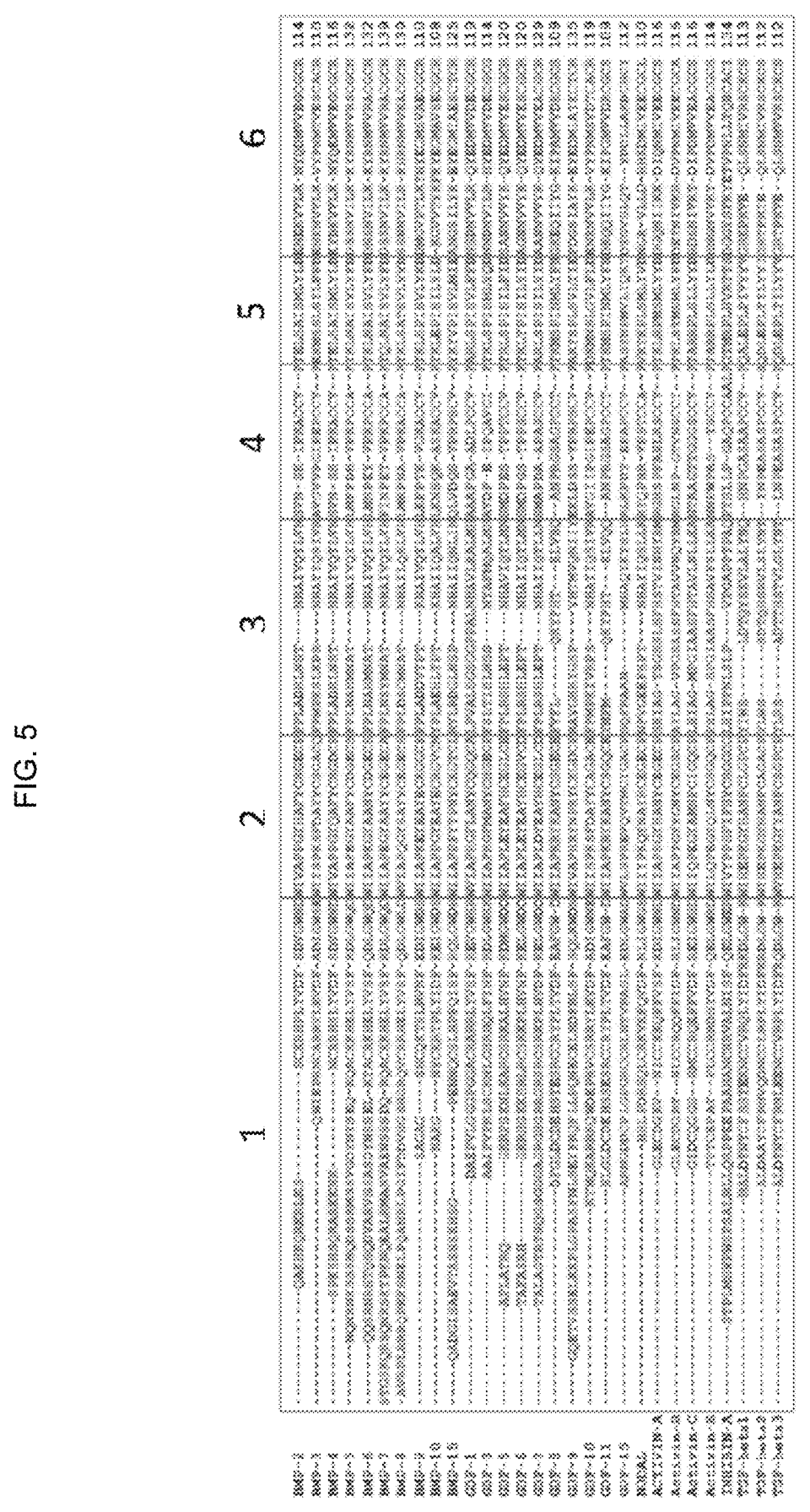

FIG. 5 shows the sequence alignment among all TGF-beta superfamily ligands as reference for the sequences of this disclosure. These are divided in their six Segments in order to illustrate their sequence and structural similarity thus to demonstrate similar design basis of DA chimeras for this superfamily.

MODE FOR THE INVENTION

Unless defined otherwise, all technical and scientific terms used herein have the same meaning as commonly understood to one of ordinary skill in the art to which this disclosure belongs. Thus, as used throughout the instant application, the following terms shall have the following meanings.

As used herein, TGF-beta superfamily member refers to a TGF-beta superfamily (including bone morphogenic factors) gene or protein of any species, particularly a mammalian species, including but not limited to bovine, ovine, porcine, murine, equine, and human. "TGF-beta superfamily polypeptide" refers to the amino acid sequences of purified TGF-beta superfamily protein obtained from any species, particularly a mammalian species, including bovine, ovine, porcine, murine, equine, and human and from any source, whether natural, synthetic, semi-synthetic, or recombinant.

"Peptide segment" refers to a portion or fragment of a larger polypeptide or protein. A peptide segment need not, on its own, have functional activity, although in some instances, a peptide segment may correspond to a domain of a polypeptide wherein the domain has its own biological activity. A stability-associated peptide segment is a peptide segment found in a polypeptide that promotes stability, function, or folding compared to a related polypeptide lacking the peptide segment.

"Fused," "operably linked," and "operably associated" are used interchangeably herein to broadly refer to a chemical or physical coupling of two otherwise distinct domains, wherein each domain has independent biological function. As such, the present disclosure provides TGF-beta (e.g., BMPs or Activins) domains that are fused to one another such that they function as a polypeptide having a TGF-beta family activity or an improvement or change in ligand specificity of a TGF-beta family of polypeptides.

"Chimera" or "chimeric protein" or "chimeric polypeptide" refers to a combination of at least two segments of at least two different parent proteins. As appreciated by one of skill in the art, the segments need not actually come from each of the parents, as it is the particular sequence that is relevant, and not the physical nucleic acids themselves. For example, a BMP chimera will have at least two segments from two different parent BMPs; or BMP and other member of the TGF-beta superfamily, or alternatively, an unrelated protein. A chimeric protein may also be an "interspecies," "intergenic," etc. fusion of protein structures (the same or different member protein) expressed by different kinds of organisms. In a preferred embodiment, two segments are connected so as to result in a new chimeric protein. In other words, a protein will not be a chimera if it has the identical sequence of either one of the full-length parents. A chimeric protein can comprise more than two segments from two different parent proteins. For example, there may be 2, 3, 4, 5, 6, or more parents for each final chimera or library of chimeras. The segment of each parent protein can be very short or very long, the segments can range in length of contiguous amino acids from 1 to about the full length of the protein. In one embodiment, the minimum length is 5 amino acids. Generally, the segment or subdomain, is one of six subdomains (see FIGS. 1 and 2).

The "six Segments" of a TGF-beta superfamily member are identified based on the structural architecture of the member protein and/or the primary amino acid sequence as aligned against other homologous member proteins, including those of other species. As identified, the member protein is generally divided into 6 distinct sections (although, alternatively, 5 distinct sections) based on segments derived to minimize alterations, or alternatively viewed, maximize alterations, to the aligned native TGF-beta member sequence during chimera engineering. Generally, FIGS. 1 and 2 show the relative positions of the distinct segments overlapping the aligned sequences of each of several TGF-beta superfamily members. Although relatively distinct, the Segments may comprise a particular amino acid sequence or an original amino acid sequence that is amenable to substitution(s), insertion(s), additional amino acid(s) at either or both termini of the original sequence, or other modifications. By "amenable", it is meant that the structural integrity of each segment is maintained as compared to the domain of the original sequence. For example, a segment described herein of a TGF-beta superfamily member may shift by 5, 3, 2, or 1, or preferably no more than 1 amino acid on either or both termini of segment as identified, for the purpose of adjoining the Segments recombinantly.

In one embodiment, the invention of a chimeric protein comprises a fusion of at least one segment from a TGF-beta member with a second segment from a second TGF-beta member, wherein the first segment is foreign to the second TGF-beta member. Utilizing the six Segments on a single subunit of the TGF-beta superfamily ligand as a scaffold framework, new (DA chimeric) sequences can be recombinantly linked by mixing segments from different TGF-beta ligands in the same order as they appear in nature. This assembly produces new sequences that are partly similar to one of several different target sequences, but distinctly different from any naturally occurring sequences.

As appreciated by one of skill in the art, "variants" of chimeras can exist as well as the exact sequences. In other words conservative amino acid substitutions may be incorporated into the chimera (e.g., from about 1-10 conservative amino acid substitutions). Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids, which encode for the same amino acids.

"Conservative" amino acid substitution refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative" substitution refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure" polypeptide refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

Table 1 shows the sequence of mature forms of TGF-beta superfamily ligands as reference for the sequences in FIG. 5 of this disclosure. The SEQ ID NOs: 14 (BMP2), 19 (BMP7), and 35 (Activin A) in this Table 1 are reproduced as their recombinantly-expressed forms as the sequence SEQ ID NOs: 5 (BMP2), 6 (BMP7), and 4 (Activin) preceded by Met as the first amino acid as described in FIG. 1(b).

TABLE 1

| TGF-b Ligand | Protein Sequence |
| --- | --- |
| BMP-2 | Qakhkqrkrlkssckrhplyvdfsdvgwndwivappgyhafychgecpfpladhlnstnhaivqtlv nsvnskipkaccvptelsaismlyldenekvvlknyqdmvvegcgcr (SEQ ID NO. 14) |
| BMP-3 (osteogenin) | Qwieprncarrylkvdfadigwsewiispksfdayycsgacqfpmpkslkpsnhatiqsivravgvv pgipepccvpekmsslsilffdenknvvlkvypnmtvescacr (SEQ ID NO. 15) |
| BMP-4 (BMP-2b) | Spkhhsqrarkknkncrrhslyvdfsdvgwndwivappgyqafychgdcpfpladhlnstnhaivq tlvnsvnssipkaccvptelsaismlyldeydkvvlknyqemvvegcgcr (SEQ ID NO. 16) |
| BMP-5 | Aanqnrnkssshqdssrmssvgdyntseqkqackkhelyvsfrdlgwqdwiiapegyaafycdg ecsfplnahmnatnhaivqtlvhlmfpdhvpkpccaptklnaisvlyfddssnvilkkyrnmvvrscg ch (SEQ ID NO. 17) |
| BMP-6 (Vgr-1) | Qqsrnrstqsqdvarvssasdynsselktacrkhelyvsfqdlgwqdwiiapkgyaanycdgecsf plnahmnatnhaivqtlvhlmnpeyvpkpccaptklnaisvlyfddnsnvilkkyrnmvvracgch SEQ ID NO. 18) |
| BMP-7 (OP-1) | Stgskqrsqnrsktpknqealrmanvaenssssdqrqackkhelyvsfrdlgwqdwiiapegyaay ycegecafplnsymnatnhaivqtlvhfinpetvpkpccaptqlnaisvlyfddssnvilkkyrnmvvr acgch (SEQ ID NO. 19) |
| BMP-8 (OP-2) | Avrplrrrqpkksnelpqanrlpgifddvhgshgrqvcrrhelyvsfqdlgwldwviapqgysayyce gecsfpldscmnatnhailqslvhlmkpnavpkaccaptklsatsvlyydssnnvilrkhrnmvvkac gch (SEQ ID NO. 20) |
| BMP-9 (GDF-2) | Sagagshcqktslrvnfedigwdswiiapkeyeayeckggcffpladdvtptkhaivqtlvhlkfptkv gkaccvptklspisvlykddmgvptlkyhyegmsvaecgcr (SEQ ID NO. 21) |
| BMP-10 | Nakgnyckrtplyidfkeigwdswiiappgyeayecrgvcnyplaehltptkhaiiqalvhlknsqkas kaccvptklepisilyldkgvvtykfkyegmaysecgcr (SEQ ID NO. 22) |
| BMP-15 (GDF-9b) | Qadgisaevtassskhsgpennqcslhpfqisfrqlgwdhwiiappfytpnyckgtclrvlrdglnspn haiiqnlinqlvdqsvprpscvpykyvpisvlmieangsilykeyegmiaesctcr (SEQ ID NO. 23) |
| GDF-1 | Daepvlgggpggacrarrlyvsfrevgwhrwviaprgflanycgqgcalpvalsgssggppalnhavl ralmhaaapgaadlpccvparlspisvlffdnsdnvvlrqyedmvvdecgc (SEQ ID NO. 24) |
| GDF-3 (Vgr-2) | Aaipvpklscknlchrhqlfinfrdlgwhkwiiapkgfmanychgecpfsltislnssnyafmqalmha vdpeipqavciptklspismlyqdnndnvilrhyedmvvdecgcg (SEQ ID NO. 25) |
| GDF-5 (BMP-14) | Aplatrqgkrpsknlkarcsrkalhvnfkdmgwddwiiapleyeafhceglcefplrshleptnhaviq tlmnsmdpestpptccvptrlspisilfidsannvvykqyedmvvescgcr (SEQ ID NO. 26) |
| GDF-6 (BMP-13) | Tafasrhgkrhgkksrlrcskkplhvnfkelgwddwiiapleyeayhcegvcdfplrshleptnhaiiqt lmnsmdpgstppsccvptkltpisilyidagnnvvykqyedmvvescgcr (SEQ ID NO. 27) |
| GDF-7 (BMP-12) | Talagtrtsqgsgggagrghgrrgrsrcsrkplhvdfkelgwddwiiapldyeayhceglcdfplrshle ptnhaiiqtllnsmapdaapasccvparlspisilyidaannvvykqyedmvveacgcr (SEQ ID NO. 28) |
| GDF-8 (Myostatin) | Dfgldcdehstesrccrypltvdfeafgwdwiiapkrykanycsgececfvflqkyphthlvhqanprgs agpcctptkmspinmlyfngkeqiiygkipamvvdrcgcs (SEQ ID NO. 29) |
| GDF-9 | Gqetvsselkkplgpasfnlseyfrqfllpqnecelhdfrlsfsqlkwdnwivaphrynpryckgdcpra vghrygspvhtmvqniiyekldssvprpscvpakysplsvltiepdgsiaykeyedmiatkctcr (SEQ ID NO. 30) |
| GDF-10(B MP-3b) | ktmqkarrkqwdeprvcsrrylkvdfadigwnewiispksfdayycagacefpmpkivrp6lsn hatiqsivravgiipgipepccvpdkmnslgvlfldenrnvvlkvypnmsvdtcacr (SEQ ID NO. 31) |
| GDF-11(B MP-11) | Nlgldcdehssesrccrypltvdfeafgwdwiiapkrykanycsgqceymfmqkyphthlvqqanp rgsagpcctptkmspinmlyfndkqqiiygkipgmvvdrcgcs (SEQ ID NO. 32) |
| GDF-15 | Arngddcplgpgrccrlhtvrasledlgwadwvlsprevqvtmcigacpsqfraanmhaqiktslhrl kpdtepapccvpasynpmvliqktdtgvslqtyddllakdchci (SEQ ID NO. 33) |
| Nodal | HHLPDRSQLCRKVKFQVDFNLIGWGSWIIYPKQYNAYRCEGECPNPVG EEFHPTNHAYIQSLLKRYQPHRVPSTCCAPVKTKPLSMLYVDNGRVLLD HHKDMIVEECGCL (SEQ ID NO. 34) |
| Activin-bA | Glecdgkvnicckkqffvsfkdigwndwiiapsgyhanycegecpshiagtsgsslsfhstvinhyr mrghspfanlksccvptklrpmsmlyyddgqniikkdiqnmiveecgcs (SEQ ID NO. 35) |
| Activin-bB | Glecdgrtnlccrqqffidfrligwndwiiaptgyygnycegscpaylagvpgsassfhtavvnqyr mrglnpgtvnscciptklstmsmlyfddeynivkrdvpnmiveecgca (SEQ ID NO. 36) |

TABLE 1-continued

| TGF-b Ligand | Protein Sequence |
|---|---|
| Activin-bC | Gidcqggsrmccrqeffvdfreigwhdwiiqpegyamnfcigqcplhiagmpgiaasfhtavlnllka ntaagttgggsccvptarrplsllyydrdsnivktdipdmvveacgcs (SEQ ID NO. 37) |
| Activin-bE | Tptcepatplccrrdhyvdfqelgwrdwilqpegyqlnycsgqcpphlagspgiaasfhsavfsllka nnpwpastsccvptarrplslyldhngnvvktdvpdmvveacgcs (SEQ ID NO. 38) |
| Inhibin-a | Stplmswpwspsalrllqrppeepaahanchrvalnisfqelgwerwivyppsfifhychggcglhip pnlslpvpgapptpaqpysllpgaqpccaalpgtmrplhvrttsdggysfkyetvpnlltqhcaci (SEQ ID NO. 39) |
| TGF-b1 | Aldtnycfssteknccvrqlyidfrkdlgwkwihepkgyhanfclgpcpyiwsldtqyskvlalynqhn pgasaapccvpqaleplpivyyvgrkpkveqlsnmivrsckcs (SEQ ID NO. 40) |
| TGF-b2 | Aldaaycfrnvqdncclrplyidfkrdlgwkwihepkgynanfcagacpylwssdtqhsrvlslyntin peasaspccvsqdleplltilyyigktpkieqlsnmivksckcs (SEQ ID NO. 41) |
| TGF-b3 | Aldtnycfrnleenccvrplyidfrqdlgwkwvhepkgyyanfcsgpcpylrsadtthstvlglyntlnp easaspccvpqdleplltilyyvgrtpkveqlsnmvyksckcs (SEQ ID NO. 42) |

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share sequence identity or sequence similarity.

"Functional" refers to a polypeptide which possesses either the native biological activity of the naturally-produced proteins of its type, or any specific desired activity, for example as judged by its ability to bind to ligand or cognate molecules.

The "Transforming Growth Factor-beta" (TGF-beta) superfamily of proteins is comprised of extracellular cytokines found in the vast majority of human cells. The TGF-beta superfamily ligands, of which there are ~40, can be subdivided into smaller families including TGF-beta, Bone Morphogenetic Proteins (BMPs), activin and inhibin, Growth and Differentiation Factors (GDFs), Nodal, Mullerian Inhibiting Substance (MIS), and Glial cell line-Derived Neurotrophic Factors (GDNFs). TGF-beta superfamily members are found in a diverse range of cell types and play roles in many fundamental cellular events including dorsal/ventral patterning and left/right axis determination to bone formation and tissue repair. More recently, several TGF-beta ligands have been shown to be involved in the maintenance or direct the differentiation of stem cells. Due to their pervasiveness, regulation of TGF-beta ligand signaling holds promise for the treatment of a wide range of different diseases from skeletal and muscle abnormalities to numerous neoplastic events. Exemplary sequences are provided herein for various members of this family or proteins, however, one of skill in the art can easily identify homologs and variants using publicly available databases by word search or sequence BLAST searches.

TGF-beta ligands are synthesized as inactive precursor molecules composed of an N-terminal pro-domain and a C-terminal mature domain linked by a protease cleavage site. To be become active, the mature domain must be cleaved from the pro-domain, commonly by a convertase, such as furin. Members of the TGF-beta superfamily are classified together due to the conserved structural architecture found in their mature domains. In general, each mature ligand monomer contains 7 cysteines, 6 of which form three intra-disulfide bonds arranged in a 'cystine knot' motif. Stretching outward from the 'cystine knot' are 4 beta strands, creating 2 curved fingers. The last remaining cysteine forms an inter-disulfide bond with a second ligand monomer, generating a covalently linked dimer. The dimer has the overall appearance of a butterfly with the 'cystine knot' as the body and the fingers spreading out like wings. The functional subunit for the TGF-beta superfamily is the dimer and they been shown to exist both as homo- and heterodimers in vivo. Some family members, such as GDF-9 and BMP-15, lack the cysteine required to form the inter-disulfide bond yet they are still able to form stable dimers.

To initiate the signaling process, TGF-beta dimers must recruit two sets of receptors, termed type I and type II. These receptors are serine/threonine kinases possessing an extracellular domain (ECD) ordered into a three-finger toxin fold, a single transmembrane domain, and a large intracellular kinase domain. TGF-beta ligands have been shown to display preferences in their affinity for the different receptor types. Activin and Nodal exhibit high affinity for type II receptors, while BMP-2 and GDF-5 possess higher affinity for type I receptors. Following the binding of two high affinity receptors to a TGF-beta ligand, two lower affinity receptors are then able to bind and join the complex. Upon binding of all four receptors to the TGF-beta ligand, forming a 6-member ternary complex, the downstream signaling cascade is initiated. The constitutively active type II receptors phosphorylate the type I receptors which, in turn, bind and phosphorylate intracellular signaling molecules called Smads. The Smad molecules then are able to translocate to the nucleus and interact directly with transcriptional regulators. Multiple mechanisms are employed to closely regulate TGF-beta signaling at different stages of the cascade: Extracellular antagonists, including Noggin, follistatin, and Inhibin; pseudo-receptors lacking the intracellular kinase domain, similar to BAMBI; or through intracellular molecules, such as inhibitory Smads.

TGF-beta superfamily ligands show a high degree of promiscuity by receptors for the ligands. While there are over 40 TGF-beta ligands, there are only 12 receptors (7 type I and 5 type II). Therefore, receptors must be able to interact with a multitude of different ligands. For instance, ActRII is known to bind Activin and BMP-7 with high affinity, but binds BMP-2 with much lower affinity. The structural details of how ligand:receptor affinity and specificity are regulated and their implications on overall signaling fate are just beginning to be understood. In GDF-5, a single amino acid has been found which determines its type I receptor preference, while in BMP-3 a single point mutation was discovered which alters type II receptor affinity as well as imparting function to the ligand. The disclosure provides methods to create modified TGF-beta ligands with novel receptor binding properties, thereby diversifying TGF-beta ligand function as well as compositions having such activity.

The disclosure provides methods of making and novel chimeric TGF-beta ligands which possess the ability to be expressed and refolded using, for example, an *E. coli* expression system. These chimeras either mimic a specific TGF-beta ligand's signaling characteristics or display unique signaling properties not seen in nature. In one embodiment, the disclosure uses Activin-betaA and BMP-7 as a template to generate an activin/BMP-7 chimera with the refolding efficiency of BMP-7 and the signaling properties of activin-betaA; however it should be recognized that any number of TGF-beta protein family members can be used.

The chimera design scheme of the disclosure yielded additional TGF-beta member chimeras (e.g., Activin/BMP-9) with new or unnatural signaling characteristics. Further, the disclosure demonstrates that a small Noggin-sensitizer section of BMP-2 or BMP-7 needs be incorporated into the target chimera to create a 'Noggin-sensitized' ligand. The invention of such chimeric TGF-beta family polypeptides provides ground to expand the library of TGF-beta ligands available for functional studies as well as facilitate the development of novel TGF-beta ligands as therapeutic agents.

The nucleic acid sequences and polypeptide sequences of BMP-2 and naturally occurring variants are known. A wild-type BMP-2 nucleic acid sequence (SEQ ID NO: 2) are provided. Met at the position N-terminal to the residue 1 (Q) results from translation of the bacterial initiation codon (ATG). Furthermore, Activin A is also known in the art (SEQ ID NO:1). This disclosure provides methods of enabling bacterial production of chimeras using a polynucleotide sequence that is codon-optimized for bacterial expression of the same polypeptide sequences of the chimeras. The disclosure also provides a number of chimeric TGF-beta family polypeptides having at least one N-terminal Segment 1 of BMP-2 or BMP-7 following Met with the initiation codon of ATG, and at least two Segments (Segments 2 and 6) derived form another TGF-beta family member, including Activin, wherein the resulting chimeric polypeptides display activities different than their parental proteins.

In one embodiment, two factors were considered when looking to design the segments of the chimeras. First was a structural consideration. The overall TGF-beta monomer fold is divided into 6 sections naturally: Beta strand 1 and 2, the pre-helix loop, alpha helix 1, and beta strand 3 and 4. The second consideration was to minimize alterations at these Segmental boundaries to the chimeras so that the regions are suitable for the overlaps in DNA sequence for PCR strategy and will minimize any changes to the natural sequences. FIG. 2 illustrates the sequence and structure of these considerations. The Segmental boundaries of the chimeras are derived from some claims priority made for those, including AB204, as illustrated in U.S. Provisional Application Ser. No. 61/155,066, filed, Feb. 24, 2009.

For example, a chimeric polypeptide comprising the algorithm 1B2B3B4B5B6A indicates 6 segments from 1 to 6, with the letter indicating the origin of the parental strand of each Segment being "A" or "B". Thus, in this example "1B2B3B4B5B6A", Segment 1 is from parental strand "B" for BMP-2 or BMP-7, for corresponding chimeras, AB215 or SAB715, respectively, Segment 2 is from parental strand "A" for Activin, Segment 3 is from parental strand "B", Segment 4 is from parental strand "B", Segment 5 is from parental strand "B", and Segment 6 is from parental strand "A".

As presented in this disclosure, it has been found that when these recombined, functional chimeric TGF-beta family polypeptides are generated, their ligand specificity can be improved or biological activity can be altered or improved compared to a unrecombined parental polypeptide. Because of differences in activity/ligand profiles, these engineered chimeric TGF-beta family polypeptides provide a unique basis to screen for activities for ligand specific activation and inhibition, provide novel therapeutic polypeptides and research reagents.

In yet another embodiment, the disclosure provides a chimeric TGF-beta polypeptide comprising a segment from Segments 2 through 6 from BMP-7 (e.g., a 1B2-BMP-7 polypeptide; see, e.g., SEQ ID NO:3), following Segment 1 from BMP2. This chimera, 1B2-BMP-7, displays a TGF-beta protein activity of BMP-7.

In some embodiments, segment of a chimeric polypeptide is 100% identical to the parental strand from which the Segment was derived. In other embodiments the segment can comprise an amino acid sequence that has at least 90%, 95%, 96%, 97%, 98%, or 99% or more identity to a corresponding Segment in a parental strand. For example, the Segment may have one or more conservative amino acid substitutions (e.g., 1-5 conservative amino acid substitutions).

In some embodiments, the biological activities of the chimeras of the disclosure can be measured using any number of recognized assays in the art for TGF-beta activity.

Such assays include, but are not limited to, BIAcore (Surface Plasmon Resonance); C2C12 luciferase assay: Smad 1/5 reporter system; HEK293 luciferase assay: Smad 2/3 reporter system; FSH (Follicle Stimulating Hormone) release assay: in rat pituitary cells; BRE (BMP Response Element) luciferase assay: Smad 1/5 reporter HEK 293 cells; Cripto binding assay: Luciferase response measured in presence/absence of Crptio; Human Stem Cell assay: cartilage regeneration assay, cartilage pellet culture ex vivo; NMR binding studies; Bone and cartilage formation measured in mice and other animals; Visualization of ligand:receptor complexes; Size Exclusion Chromatography (SEC; Velocity Scan Ultracentrifugation to visualize ligand:receptor complex formation; and Seldi mass Spectrometry to accurately determine size of ligands.

Modified chimeras can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

In certain embodiments, the present invention contemplates making mutations in the proteolytic cleavage site of the chimera sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the chimera sequences so as to alter the glycosylation of the chimera. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid), which is specifically recognized by appropriate cellular glycosylation enzymes. The alteration may also be made by the addition of, or substitution by, one or more serine or threonine residues to the sequence of the wild-type polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties is by chemical or enzymatic coupling of glycosides to the polypeptide.

The disclosure also provides polynucleotides encoding some of the chimeric polypeptides disclosed herein. The polynucleotides may be codon-optimized and operably linked to one or more heterologous regulatory or control sequences that control gene expression to create a recombinant polynucleotide capable of expressing the polypeptide in particular expression hosts. Expression constructs containing any polynucleotides encoding the chimeric polypeptide can be reasonably designed to introduce them into appropriate host cells to express the chimeric polypeptides.

Given the knowledge of specific sequences of the TGF-beta family of proteins, and the specific descriptions of the chimeric polypeptides herein (e.g., the segment structure of the chimeric domains), the nucleic acid sequence of the engineered chimera will be apparent to the skilled artisan. The knowledge of the codons corresponding to various amino acids coupled with the knowledge of the amino acid sequence of the polypeptides allows those skilled in the art to make different polynucleotides encoding the same polypeptides of the disclosure. Thus, the present disclosure contemplates each and every possible variation of the polynucleotides that could be made by selecting combinations based on possible codon choices, and all such variations are to be considered specifically disclosed for any of the polypeptides described herein.

While one example of an expression system discussed is an *E. coli* expression system, to those skilled in the art, these proteins can be easily be cloned into and expressed from a large number of other expression systems. The advantages include, but are not limited to, achieving post-translational modifications as would be seen in the organism the protein was derived from (in this case *H. sapiens*), expression of the ligands without the start methionine required for bacterial expression, and easy incorporation of non-natural amino acids or additional chemical modifications. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). In addition to prokaryotes, eukaryotic microbes such as filamentous fungi or yeast are suitable cloning or expression hosts for VEGF-E-encoding vectors. *Saccharomyces cerevisiae* is a commonly used lower eukaryotic host microorganism.

Suitable host cells for the expression of invention chimeras are derived from unicellular and multicellular organisms. Examples of invertebrate cells include insect cells such as *Drosophila* S2 and *Spodoptera* Sf9, as well as plant cells. Plant expression systems have also been used successfully to express modified proteins. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Alternate protein expression systems include human embryonic kidney (HEK) 293 cells, insect cell line (*S. frugiperda*) utilizing the baculovirus expression system, yeast expression systems not limited to *P. pastoris* and *S. cerevisiae*, and numerous Microalgae strains. Transgenic animals can be used to express correctly modified protein. In essence, the animals become living 'bioreactors' capable of expressing large amounts of the desired protein in an easily harvested fluid or tissue, such as the milk from a cow. Cell-free in vitro expression systems using either the bacterial or wheat germ cell lysate can be employed. Cell-free expression system will permit inserting a wide range of non-natural amino acids or epitope tags with higher efficiency and greater specificity.

In certain aspects, the present disclosure provides methods and agents for stimulating cartilage and bone formation and increasing their mass. Therefore, any chimeric protein of the disclosure that is expected to affect bone-related function of a TGF-beta superfamily protein such as for example BMP-2, BMP-3, GDF-10, BMP-4, BMP-7, or BMP-8, can be tested in whole cells or tissues, in vitro or in vivo, to confirm their ability to modulate bone or cartilage growth. Various methods known in the art can be utilized for this purpose. Thus, the effect of a subject chimera, preferably one comprising a Segment from a BMP-2, BMP-3 or BMP-7, on bone or cartilage growth can be determined by their effect on the osteogenic and chondrogenic activities, for example, by measuring ostengenic induction of Msx2 or positive or negative differentiation marker genes of chondrogenesis, including ACAN (positive), Col2A1 (positive), MMP13 (negative), ADAMTS-5 (negative), and ColX (negative), in cell based assays (see also, e.g., Daluiski et al., Nat. Genet. 2001, 27(1): 84-8; Hino et al., Front Biosci. 2004, 9:1520-9).

It is understood that the screening assays of the present disclosure apply to not only the subject chimeric proteins and variants thereof, but also any test compounds including agonists and antagonist of the chimeric proteins or their variants themselves as references. Further, these screening assays are useful for drug target verification and quality control purposes.

Chimeras of the disclosure may be formulated for use in various biological systems in vitro and in vivo. Any of a variety of art-known methods can be used to administer a chimera either alone or in combination with other active agents. For example, administration can be parenterally by injection or by gradual infusion to the tissue area over time. The agent(s) can be administered by such means as oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, intracavity, and inhalation administration, administration to the liver by intraportal delivery, as well as direct organ injection (e.g., into the liver, into the brain for delivery to the central nervous system, into the pancreas). The most suitable route in any given case will depend on the nature and severity of the condition being treated and on the nature of the particular compound that is being used.

The disclosure also provides a pharmaceutical preparation comprising a subject chimeric protein and a pharmaceutically acceptable carrier. A pharmaceutical preparation may be employed to promote growth of a tissue or diminishing or prevent loss of a tissue in a subject, preferably a human. The targeted tissue can be, for example, bone, cartilage, joint, skeletal muscle, cardiac muscle or neuronal tissue.

In another aspect, a chimera can be formulated either alone or in combination with other agents for administration (e.g., as a lotion, cream, spray, gel, or ointment). It may be formulated into liposomes to reduce toxicity or increase bioavailability. Other methods for delivery include oral methods that entail encapsulation of the in microspheres or proteinoids, aerosol delivery (e.g., to the lungs), or transdermal delivery (e.g., by iontophoresis or transdermal electroporation). Other methods of administration will be known to those skilled in the art.

EXAMPLES

Example 1

Generation of TGF-beta Chimeras. To be broadly applicable as the design principle, it is also part of the design to keep two structural segments, sections 3 and 4, can be treated as one section of either of the parental gene (referred to as section 3*4). The strategy was implemented originally by making Activin/BMP-2 chimeras using activin-betaA as a target ligand and BMP-2 as the backbone ligand. This invention has been previously filed, examined, and published, which claims priority under 35 U.S.C. § 119 to U.S. Provisional Application Ser. No. 61/155,066, filed, Feb. 24, 2009, entitled as "Designer Ligands of TGG-beta Superfamily Ligands".

For the Activin/BMP-2 chimeras, the mature domains of human BMP-2 and human activin-betaA were previously divided into 6 Segments each, and primers were designed for each Segment. For BMP-2, the primers coded for the following six Segments have been designed. The six-residues-long Noggin-sensitizer sequence within Segment 6 is underlined.

```
Segment 1,
                                 (SEQ ID NO: 46)
QAKHKQRKRLKSSCKRHPLYVDFSDVGWND;

Segment 2,
                                 (SEQ ID NO: 47)
WIVAPPGYHAFYCHGECP;

Segment 3,
                                 (SEQ ID NO: 48)
FPLADHLNSTNHAIVQTLVN;

Segment 4,
                                 (SEQ ID NO: 49)
SVNSKIPKACCVP;

Segment 5,
                                 (SEQ ID NO: 50)
TELSAISMLYYD;

Segment 6,
                                 (SEQ ID NO: 51)
ENEKVVLKNYQDMVVEGCGCR.
```

For Activin-betaA, the primers coded for the following six Segments have been designed. The six-residues-long Noggin-sensitizer sequence within Segment 6 is underlined.

```
Segment 1,
                                 (SEQ ID NO: 52)
RGLECDGKVNICCKKQFFVSFKDIGWNDW;

Segment 2,
                                 (SEQ ID NO: 53)
WIIAPSGYHANYCEGECP;

Segment 3,
                                 (SEQ ID NO: 54)
SHIAGTSGSSLSFHSTLVN;

Segment 4,
                                 (SEQ ID NO: 55)
HYRMRGHSPFANLKSCCVP;

Segment 5,
                                 (SEQ ID NO: 56)
TKLRPMSMLYYD;

Segment 6,
                                 (SEQ ID NO: 57)
DGQNIIKKDIQNMIVEECGCS.
```

An overlapping PCR strategy was used to mix the various Segments of BMP-2 and Activin-betaA operably linked in the order of 1, 2, 3, 4, 5, and 6 following the initiation codon ATG for Met, to generate full-length chimeras.

For the Activin/BMP-7 chimeras, the mature domains of human BMP-7 and human Activin-betaA were initially divided into 6 Segments each, and their primers were designed for each Segment. For BMP-7, the primers coded for the following protein sequences have been designed. The six-residues-long Noggin-sensitizer sequence within Segment 6 is underlined.

```
Segment 1,
                                    (SEQ ID NO: 58)
MSTGSKQRSQNRSKTPKNQEALRMANVAENSSSDQRQACKKHE-
LYVSFRDLGWQD Segment 2,
                                    (SEQ ID NO: 59)
WIIAPEGYAAYYCEGECA;

Segment 3,
                                    (SEQ ID NO: 60)
GPLNSYMNATNHAIVQTLVH;

Segment 4,
                                    (SEQ ID NO: 61)
FINPETVPKPCCAP;

Segment 5,
                                    (SEQ ID NO: 62)
TQLNAISVLYFD;

Segment 6,
                                    (SEQ ID NO: 63)
DSSNVILKKYRNMVVRACGCH;
```

For Activin-betaA, the primers coded for the following six Segments have been designed. The six-residues-long Noggin-sensitizer sequence within Segment 6 is underlined.

```
Segment 1,
                                    (SEQ ID NO: 52)
RGLECDGKVNICCKKQFFVSFKDIGWNDW;

Segment 2,
                                    (SEQ ID NO: 53)
WIIAPSGYHANYCEGECP;

Segment 3,
                                    (SEQ ID NO: 54)
SHIAGTSGSSLSFHSTLVN;

Segment 4,
                                    (SEQ ID NO: 55)
HYRMRGHSPFANLKSCCVP;

Segment 5,
                                    (SEQ ID NO: 56)
TKLRPMSMLYYD;

Segment 6,
                                    (SEQ ID NO: 57)
DGQNIIKKDIQNMIVEECGCS.
```

An overlapping PCR strategy was used to mix the various Segments of BMP-7 and Activin-betaA operably linked in the order of 1, 2, 3, 4, 5, and 6 following the initiation codon ATG for Met, to generate full-length chimeras.

To generate the 1B2 chimera of BMP-7, 1B2-BMP-7, two oligos were used to insert the BMP-2 Segment 1 followed by two amino acids, II (underlined), QAKHKQRKRLKSSCK-RHPLYVDFSDVGWNDII (SEQ ID NO: 64), into the target gene.

Two amino acids, II, were added to create a convenient restriction enzyme site. Outer primers for all constructs were constructed to incorporate a 5' NdeI site and a 3' XhoI site for cloning into pET21a expression vector. FIG. 2 describes 1B2-BMP-7 as below, which sets the basis of various chimeras and their variants, including 1B2-NAB704 and 1B2-AB704 and 1B2-NAB715, using this N-terminal addition of 1B2 Segment. These two amino acids added to the C-terminus of Segment 1 are, however, not required to create 1B2-BMP7. Both sequences are operably equal.

```
Segment 1,
                                    (SEQ ID NO: 64)
QAKHKQRKRLKSSCKRHPLYVDFSDVGWNDII; (BMP-2)

Segment 2,
                                    (SEQ ID NO: 59)
WIIAPEGYAAYYCEGECA; (BMP-7)

Segment 3,
                                    (SEQ ID NO: 60)
GPLNSYMNATNHAIVQTLVH; (BMP-7)

Segment 4,
                                    (SEQ ID NO: 61)
FINPETVPKPCCAP (BMP-7)

Segment 5,
                                    (SEQ ID NO: 62)
TQLNAISVLYFD (BMP-7)

Segment 6,
                                    (SEQ ID NO: 63)
DSSNVILKKYRNMVVRACGCH (BMP-7)
```

Protein Expression and Purification. Activin/BMP-2 chimeras, Activin/BMP-7 chimeras, Activin-betaA, 1B chimeras, and their Noggin-sensitized variants were expressed using a typical *E. coli* expression system, and chimeras were found in the inclusion body fractions. The expressed inclusion bodies were isolated, purified, and refolded. The refolded ligands were purified using a Hi-trap heparin column (GE Healthcare) and reversed phase chromatography (GraceVydac). The ligands were lyophilized and re-suspended in 4 mM HCl, pH 1 for use in all cell based assays or 10 mM Na acetate, pH 4 for all biophysical assays. Some of these were expressed in a stably transfected CHO cell line and purified using techniques known in the art. Noggin was expressed and purified based on previously described protocols.

Smad-1 Luciferase Assays in C2C12 Cells. Smad1-dependent luciferase assays were performed using techniques known in the art. In brief, C2C12 myoblast cells are cultured in Dulbecco's minimum essential medium (DMEM)+5% FBS supplemented with L-Glutamine and antibiotics. For luciferase reporter assays, cells were trypsinized, washed twice with PBS and plated into 48-well plates with DMEM+ 0.1% FBS. Luciferase activity was measured 24 hours after stimulation with ligands and the values were normalized for transfection efficiency by using beta-galactosidase activity. The activity of the luciferase reporter is expressed in fold-induction relative to control values that are obtained by using-927Id1-luciferase that lacks Smad binding domains (Id1-Luc mut). To test for the ability of Noggin to attenuate the Smad1 signaling of the ligands, the luciferase assays were repeated as described above, with a set dose of Noggin included in the assay. FIG. 3 illustrates that SAB704 has the signaling ability approximately 30-fold higher than that of natural BMP-7 based on their ED50s of 15.6 nM and 423.1 nM, respectively. FIG. 4(a) illustrates that these activities are associated with the enhanced RNA-induction activity of SAB704 by increasing cartilage-promoting gene expression, including aggrecan and COL2A1, or decreasing hypertrophic genes, including ADAMTS5, COLX, and MMP13 shown in FIGS. 4(*b*) through 4(*i*).

Smad-2 Luciferase Assays in HEK293 Cells. HEK293T cells were seeded into 24-well plates coated with polylysine at a density of 150,000 cells/well. After 24 h cells were transfected overnight with a mixture of A3 Lux (25 ng) and beta-galactosidase (25 ng) reporter plasmids, the transcription factor FAST2 (50 ng), and empty pCDNA3 vector (400 ng) using Perfectin® transfection reagent (GenLantis) according to the manufacturer's recommendations. Then the cells were treated with increasing doses of activin-betaA or activin/BMP-2 chimeras for 16-24 h. The cells were harvested in ice-cold lysis buffer (1% Triton X-100 in 25 mM glycylglycine, 4 nM EGTA, 15 mM $MgSO_4$ containing 1 mM dithiothreitol) and assayed for luciferase and beta-galactosidase activities using standard methods. To assess the ability of the chimeras to bind known TGF-beta co-receptors, the HEK293T cells were treated with increasing doses of activin-betaA or Activin/BMP-7 chimeras. Activity was then measures as previously described.

Noggin insensitivity of AB204, SAB704, and SAB715. Noggin suppresses the signaling activity by directly complexing with the ligand, and rendering it unable to bind its own receptors for signaling. As a result, in contrast to BMP-2, which is blocked to near background levels in the presence of Noggin, the higher signaling of AB204, SAB704, and SAB715, are not expected to be inhibited by Noggin. FIG. 4 illustrates that their cellular activities of Noggin-sensitive BMP2, or Noggin-sensitive BMP7, or Noggin-insensitive AB204, or Noggin-insensitive SAB704, or SAB715. FIG. 4(*b*) illustrates the size-exclusion chromatography of NAB204 to demonstrate its physical binding to Noggin as compared to AB204 that is incapable of binding Noggin. This physical binding provides direct explanation for the Noggin-insensitivity of the signaling activities of AB204, and thus of SAB704, and SAB715. This property makes them particularly powerful in modulating their cellular signaling ability of in vivo activity by time-dependent combinatorial mix among them, including for bone and cartilage regeneration.

This application contains references to amino acid sequences and/or nucleic acid sequences which have been submitted herewith as the sequence listing text file entitled "000151usnp_SequenceLisiting_revised_ST25.txt", file size 52,769 Bytes (B), created on 4 Nov. 2024. The aforementioned sequence listing is hereby incorporated by reference in its entirety pursuant to 37 C.F.R. § 1.52(e).

The invention claimed is:

1. A recombinant polypeptide comprising an amino acid selected from the group consisting of SEQ ID NO: 8, SEQ ID NO: 10 and SEQ ID NO: 12, wherein the recombinant polypeptide modulates the SMAD pathway.

2. A polynucleotide encoding the recombinant polypeptide of claim 1.

3. A vector comprising the polynucleotide of claim 2.

4. A host cell genetically encoding or comprising the vector of claim 3.

5. A pharmaceutical composition comprising the recombinant polypeptide of claim 1.

* * * * *

SEQUENCE LISTING

```
<160> NUMBER OF SEQ ID NOS: 64

<210> SEQ ID NO 1
<211> LENGTH: 345
<212> TYPE: DNA
<213> ORGANISM: Artificial Sequence
<220> FEATURE:
<223> OTHER INFORMATION: Activin A

<400> SEQUENCE: 1
atgcaagcca aacacaaaca gcggaagcgt cttaagtcca gctgcaaaag gcaccctttg      60
tatgtggact tcagtgatgt ggggtggaat gactggatca ttgctccctc tggctatcat     120
gccaactact gcgacggaga atgccctttt cctctggctg atcatctgaa ctccactaat     180
catgccattg ttcagacgtt ggtcaactct gttaactcta agattcctaa ggcatgctgt     240
gtcccgacca agctgagacc catgtccatg ttgtactatg atgatggtca aaacatcatc     300
aaaaaggaca ttcagaacat gatcgtggag gagtgtgggt gctca                     345

<210> SEQ ID NO 2
<211> LENGTH: 345
<212> TYPE: DNA
<213> ORGANISM: Artificial Sequence
<220> FEATURE:
<223> OTHER INFORMATION: BMP2

<400> SEQUENCE: 2
atgcaagcca aacacaaaca gcggaagcgt cttaagtcca gctgcaaaag gcaccctttg      60
tatgtggact tcagtgatgt ggggtggaat gactggatca ttgctccctc tggctatcat     120
gccaactact gcgacggaga atgccctttt cctctggctg atcatctgaa ctccactaat     180
catgccattg ttcagacgtt ggtcaactct gttaactcta agattcctaa ggcatgctgt     240
gtcccgacca agctgagacc catgtccatg ttgtactatg atgatggtca aaacatcatc     300
aaaaaggaca ttcagaacat gatcgtggag gagtgtgggt gctca                     345

<210> SEQ ID NO 3
```

-continued

```
<211> LENGTH: 348
<212> TYPE: DNA
<213> ORGANISM: Artificial Sequence
<220> FEATURE:
<223> OTHER INFORMATION: 1B2-BMP-7

<400> SEQUENCE: 3
atgcaagcca aacacaaaca gcggaaacgc cttaagtcca gctgtaagag acaccctttg      60
tacgtggact tcagtgacgt ggggtggaat gactggatta tcgcgcctga aggctacgcc     120
gcctactact gtgaggggga gtgtgccttc cctctgaact cctacatgaa cgccaccaac     180
cacgccatcg tgcagacgct ggtccacttc atcaacccgg aaacggtgcc caagccctgc     240
tgtgcgccca cgcagctcaa tgccatctcc gtcctctact cgatgacag ctccaacgtc      300 atcctgaaga aatacagaaa catggtggtc cgggcctgtg ctgccac                  348

<210> SEQ ID NO 4
<211> LENGTH: 117
<212> TYPE: PRT
<213> ORGANISM: Artificial Sequence
<220> FEATURE:
<223> OTHER INFORMATION: Activin A

<400> SEQUENCE: 4

Met Gly Leu Glu Cys Asp Gly Lys Val Asn Ile Cys Cys Lys Lys Gln
1               5                   10                  15

Phe Phe Val Ser Phe Lys Asp Ile Gly Trp Asn Asp Trp Ile Ile Ala
            20                  25                  30

Pro Ser Gly Tyr His Ala Asn Tyr Cys Glu Gly Glu Cys Pro Ser His
        35                  40                  45

Ile Ala Gly Thr Ser Gly Ser Ser Leu Ser Phe His Ser Thr Val Ile
        50                  55                  60

Asn His Tyr Arg Met Arg Gly His Ser Pro Phe Ala Asn Leu Lys Ser
65                  70                  75                  80

Cys Cys Val Pro Thr Lys Leu Arg Pro Met Ser Met Leu Tyr Tyr Asp
                85                  90                  95

Asp Gly Gln Asn Ile Ile Lys Lys Asp Ile Gln Asn Met Ile Val Glu
            100                 105                 110

Glu Cys Gly Cys Ser
        115

<210> SEQ ID NO 5
<211> LENGTH: 115
<212> TYPE: PRT
<213> ORGANISM: Artificial Sequence
<220> FEATURE:
<223> OTHER INFORMATION: BMP 2

<400> SEQUENCE: 5

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Val Ala Pro Pro Gly Tyr His Ala Phe Tyr Cys His Gly Glu Cys
        35                  40                  45

Pro Phe Pro Leu Ala Asp His Leu Asn Ser Thr Asn His Ala Ile Val
        50                  55                  60

Gln Thr Leu Val Asn Ser Val Asn Ser Lys Ile Pro Lys Ala Cys Cys
65                  70                  75                  80
```

```
Val Pro Thr Glu Leu Ser Ala Ile Ser Met Leu Tyr Leu Asp Glu Asn
            85                  90                  95

Glu Lys Val Val Leu Lys Asn Tyr Gln Asp Met Val Val Glu Gly Cys
            100                 105                 110

Gly Cys Arg
        115

<210> SEQ ID NO 6
<211> LENGTH: 140
<212> TYPE: PRT
<213> ORGANISM: Artificial Sequence
<220> FEATURE:
<223> OTHER INFORMATION: BMP 7

<400> SEQUENCE: 6

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Glu Gly Tyr Ala
        50                  55                  60

Ala Tyr Tyr Cys Glu Gly Glu Cys Ala Phe Pro Leu Asn Ser Tyr Met
65                  70                  75                  80

Asn Ala Thr Asn His Ala Ile Val Gln Thr Leu Val His Phe Ile Asn
            85                  90                  95

Pro Glu Thr Val Pro Lys Pro Cys Cys Ala Pro Thr Gln Leu Asn Ala
            100                 105                 110

Ile Ser Val Leu Tyr Phe Asp Asp Ser Ser Asn Val Ile Leu Lys Lys
        115                 120                 125

Tyr Arg Asn Met Val Val Arg Ala Cys Gly Cys His
    130                 135                 140

<210> SEQ ID NO 7
<211> LENGTH: 115
<212> TYPE: PRT
<213> ORGANISM: Artificial Sequence
<220> FEATURE:
<223> OTHER INFORMATION: AB204

<400> SEQUENCE: 7

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
            20                  25                  30

Ile Ile Ala Pro Ser Gly Tyr His Ala Asn Tyr Cys Asp Gly Glu Cys
        35                  40                  45

Pro Phe Pro Leu Ala Asp His Leu Asn Ser Thr Asn His Ala Ile Val
        50                  55                  60

Gln Thr Leu Val Asn Ser Val Asn Ser Lys Ile Pro Lys Ala Cys Cys
65                  70                  75                  80

Val Pro Thr Lys Leu Arg Pro Met Ser Met Leu Tyr Tyr Asp Asp Gly
            85                  90                  95

Gln Asn Ile Ile Lys Lys Asp Ile Gln Asn Met Ile Val Glu Glu Cys
            100                 105                 110

Gly Cys Ser
        115
```

```
<210> SEQ ID NO 8
<211> LENGTH: 115
<212> TYPE: PRT
<213> ORGANISM: Artificial Sequence
<220> FEATURE:
<223> OTHER INFORMATION: NAB204

<400> SEQUENCE: 8

Met Gln Ala Lys His Lys Gln Arg Lys Arg Leu Lys Ser Ser Cys Lys
1               5                   10                  15

Arg His Pro Leu Tyr Val Asp Phe Ser Asp Val Gly Trp Asn Asp Trp
                20                  25                  30

Ile Ile Ala Pro Ser Gly Tyr His Ala Asn Tyr Cys Asp Gly Glu Cys
            35                  40                  45

Pro Phe Pro Leu Ala Asp His Leu Asn Ser Thr Asn His Ala Ile Val
        50                  55                  60

Gln Thr Leu Val Asn Ser Val Asn Ser Lys Ile Pro Lys Ala Cys Cys
65                  70                  75                  80

Val Pro Thr Lys Leu Arg Pro Met Ser Met Leu Tyr Tyr Asp Asp Gly
                85                  90                  95

Gln Asn Val Val Leu Lys Asn Tyr Gln Asn Met Ile Val Glu Glu Cys
                100                 105                 110

Gly Cys Ser
        115

<210> SEQ ID NO 9
<211> LENGTH: 140
<212> TYPE: PRT
<213> ORGANISM: Artificial Sequence
<220> FEATURE:
<223> OTHER INFORMATION: SAB704

<400> SEQUENCE: 9

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
                20                  25                  30

Ser Asp Gln Arg Gln Ala Cys Lys Lys His Glu Leu Tyr Val Ser Phe
            35                  40                  45

Arg Asp Leu Gly Trp Gln Asp Trp Ile Ile Ala Pro Ser Gly Tyr His
        50                  55                  60

Ala Asn Tyr Cys Glu Gly Glu Cys Pro Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Lys Leu Arg Pro
                100                 105                 110

Met Ser Met Leu Tyr Tyr Asp Asp Gly Gln Asn Ile Ile Lys Lys Asp
        115                 120                 125

Ile Gln Asn Met Ile Val Glu Glu Cys Gly Cys Ser
        130                 135                 140

<210> SEQ ID NO 10
<211> LENGTH: 140
<212> TYPE: PRT
<213> ORGANISM: Artificial Sequence
<220> FEATURE:
<223> OTHER INFORMATION: NAB704
```

```
<400> SEQUENCE: 10

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Ser Gly Tyr His
        50                  55                  60

Ala Asn Tyr Cys Glu Gly Glu Cys Pro Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Lys Leu Arg Pro
                100                 105                 110

Met Ser Met Leu Tyr Tyr Asp Asp Gly Gln Asn Val Ile Leu Lys Lys
            115                 120                 125

Tyr Gln Asn Met Ile Val Glu Glu Cys Gly Cys Ser
        130                 135                 140

<210> SEQ ID NO 11
<211> LENGTH: 140
<212> TYPE: PRT
<213> ORGANISM: Artificial Sequence
<220> FEATURE:
<223> OTHER INFORMATION: SAB715

<400> SEQUENCE: 11

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
            20                  25                  30

Ser Asp Gln Arg Gln Ala Cys Lys Lys His Glu Leu Tyr Val Ser Phe
        35                  40                  45

Arg Asp Leu Gly Trp Gln Asp Trp Ile Ile Ala Pro Ser Gly Tyr His
        50                  55                  60

Ala Asn Tyr Cys Glu Gly Glu Cys Pro Phe Pro Leu Asn Ser Tyr Met
65                  70                  75                  80

Asn Ala Thr Asn His Ala Ile Val Gln Thr Leu Val His Phe Ile Asn
                85                  90                  95

Pro Glu Thr Val Pro Lys Pro Cys Cys Ala Pro Thr Gln Leu Asn Ala
                100                 105                 110

Ile Ser Val Leu Tyr Phe Asp Asp Gly Gln Asn Ile Ile Lys Lys Asp
            115                 120                 125

Ile Gln Asn Met Ile Val Glu Glu Cys Gly Cys Ser
        130                 135                 140

<210> SEQ ID NO 12
<211> LENGTH: 140
<212> TYPE: PRT
<213> ORGANISM: Artificial Sequence
<220> FEATURE:
<223> OTHER INFORMATION: NAB715

<400> SEQUENCE: 12

Met Ser Thr Gly Ser Lys Gln Arg Ser Gln Asn Arg Ser Lys Thr Pro
1               5                   10                  15
```

```
Lys Asn Gln Glu Ala Leu Arg Met Ala Asn Val Ala Glu Asn Ser Ser
            20              25              30

Ser Asp Gln Arg Gln Ala Cys Lys Lys His Glu Leu Tyr Val Ser Phe
            35              40              45

Arg Asp Leu Gly Trp Gln Asp Trp Ile Ile Ala Pro Ser Gly Tyr His
    50              55              60

Ala Asn Tyr Cys Glu Gly Glu Cys Pro Phe Pro Leu Asn Ser Tyr Met
65              70              75              80

Asn Ala Thr Asn His Ala Ile Val Gln Thr Leu Val His Phe Ile Asn
                85              90              95

Pro Glu Thr Val Pro Lys Pro Cys Cys Ala Pro Thr Gln Leu Asn Ala
            100             105             110

Ile Ser Val Leu Tyr Phe Asp Asp Gly Gln Asn Val Ile Leu Lys Asn
            115             120             125

Tyr Gln Asn Met Ile Val Glu Glu Cys Gly Cys Ser
    130             135             140

<210> SEQ ID NO 13
<211> LENGTH: 116
<212> TYPE: PRT
<213> ORGANISM: Artificial Sequence
<220> FEATURE:
<223> OTHER INFORMATION: 1B2BMP7

<400> SEQUENCE: 13

Met Gln Ala Lys His Lys Gln Arg Lys Arg Leu Lys Ser Ser Cys Lys
1               5               10              15

Arg His Pro Leu Tyr Val Asp Phe Ser Asp Val Gly Trp Asn Asp Trp
            20              25              30

Ile Ile Ala Pro Glu Gly Tyr Ala Ala Tyr Tyr Cys Glu Gly Glu Cys
            35              40              45

Ala Phe Pro Leu Asn Ser Tyr Met Asn Ala Thr Asn His Ala Ile Val
    50              55              60

Gln Thr Leu Val His Phe Ile Asn Pro Glu Thr Val Pro Lys Pro Cys
65              70              75              80

Cys Ala Pro Thr Gln Leu Asn Ala Ile Ser Val Leu Tyr Phe Asp Asp
                85              90              95

Ser Ser Asn Val Ile Leu Lys Lys Tyr Arg Asn Met Val Val Arg Ala
            100             105             110

Cys Gly Cys His
        115

<210> SEQ ID NO 14
<211> LENGTH: 114
<212> TYPE: PRT
<213> ORGANISM: Artificial Sequence
<220> FEATURE:
<223> OTHER INFORMATION: BMP-2

<400> SEQUENCE: 14

Gln Ala Lys His Lys Gln Arg Lys Arg Leu Lys Ser Ser Cys Lys Arg
1               5               10              15

His Pro Leu Tyr Val Asp Phe Ser Asp Val Gly Trp Asn Asp Trp Ile
            20              25              30

Val Ala Pro Pro Gly Tyr His Ala Phe Tyr Cys His Gly Glu Cys Pro
            35              40              45

Phe Pro Leu Ala Asp His Leu Asn Ser Thr Asn His Ala Ile Val Gln
```

-continued

```
         50              55              60

Thr Leu Val Asn Ser Val Asn Ser Lys Ile Pro Lys Ala Cys Cys Val
65              70              75              80

Pro Thr Glu Leu Ser Ala Ile Ser Met Leu Tyr Leu Asp Glu Asn Glu
                85              90              95

Lys Val Val Leu Lys Asn Tyr Gln Asp Met Val Val Glu Gly Cys Gly
            100             105             110

Cys Arg

<210> SEQ ID NO 15
<211> LENGTH: 110
<212> TYPE: PRT
<213> ORGANISM: Artificial Sequence
<220> FEATURE:
<223> OTHER INFORMATION: BMP-3 (osteogenin)

<400> SEQUENCE: 15

Gln Trp Ile Glu Pro Arg Asn Cys Ala Arg Arg Tyr Leu Lys Val Asp
1               5               10              15

Phe Ala Asp Ile Gly Trp Ser Glu Trp Ile Ile Ser Pro Lys Ser Phe
                20              25              30

Asp Ala Tyr Tyr Cys Ser Gly Ala Cys Gln Phe Pro Met Pro Lys Ser
            35              40              45

Leu Lys Pro Ser Asn His Ala Thr Ile Gln Ser Ile Val Arg Ala Val
        50              55              60

Gly Val Val Pro Gly Ile Pro Glu Pro Cys Cys Val Pro Glu Lys Met
65              70              75              80

Ser Ser Leu Ser Ile Leu Phe Phe Asp Glu Asn Lys Asn Val Val Leu
                85              90              95

Lys Val Tyr Pro Asn Met Thr Val Glu Ser Cys Ala Cys Arg
            100             105             110

<210> SEQ ID NO 16
<211> LENGTH: 116
<212> TYPE: PRT
<213> ORGANISM: Artificial Sequence
<220> FEATURE:
<223> OTHER INFORMATION: BMP-4(BMP-2b)

<400> SEQUENCE: 16

Ser Pro Lys His His Ser Gln Arg Ala Arg Lys Lys Asn Lys Asn Cys
1               5               10              15

Arg Arg His Ser Leu Tyr Val Asp Phe Ser Asp Val Gly Trp Asn Asp
                20              25              30

Trp Ile Val Ala Pro Pro Gly Tyr Gln Ala Phe Tyr Cys His Gly Asp
            35              40              45

Cys Pro Phe Pro Leu Ala Asp His Leu Asn Ser Thr Asn His Ala Ile
        50              55              60

Val Gln Thr Leu Val Asn Ser Val Asn Ser Ser Ile Pro Lys Ala Cys
65              70              75              80

Cys Val Pro Thr Glu Leu Ser Ala Ile Ser Met Leu Tyr Leu Asp Glu
                85              90              95

Tyr Asp Lys Val Val Leu Lys Asn Tyr Gln Glu Met Val Val Glu Gly
            100             105             110

Cys Gly Cys Arg
        115
```

<210> SEQ ID NO 17
<211> LENGTH: 134
<212> TYPE: PRT
<213> ORGANISM: Artificial Sequence
<220> FEATURE:
<223> OTHER INFORMATION: BMP-5

<400> SEQUENCE: 17

Ala Ala Asn Gln Asn Arg Asn Lys Ser Ser Ser His Gln Asp Ser Ser
1               5                   10                  15

Arg Met Ser Ser Val Gly Asp Tyr Asn Thr Ser Glu Gln Lys Gln Ala
            20                  25                  30

Cys Lys Lys His Glu Leu Tyr Val Ser Phe Arg Asp Leu Gly Trp Gln
        35                  40                  45

Asp Trp Ile Ile Ala Pro Glu Gly Tyr Ala Ala Phe Tyr Cys Asp Gly
    50                  55                  60

Glu Cys Ser Phe Pro Leu Asn Ala His Met Asn Ala Thr Asn His Ala
65                  70                  75                  80

Ile Val Gln Thr Leu Val His Leu Met Phe Pro Asp His Val Pro Lys
                85                  90                  95

Pro Cys Cys Ala Pro Thr Lys Leu Asn Ala Ile Ser Val Leu Tyr Phe
            100                 105                 110

Asp Asp Ser Ser Asn Val Ile Leu Lys Lys Tyr Arg Asn Met Val Val
        115                 120                 125

Arg Ser Cys Gly Cys His
    130

<210> SEQ ID NO 18
<211> LENGTH: 132
<212> TYPE: PRT
<213> ORGANISM: Artificial Sequence
<220> FEATURE:
<223> OTHER INFORMATION: BMP-6(Vgr-1)

<400> SEQUENCE: 18

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
            20                  25                  30

Lys His Glu Leu Tyr Val Ser Phe Gln Asp Leu Gly Trp Gln Asp Trp
        35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

Asn Ser Asn Val Ile Leu Lys Lys Tyr Arg Asn Met Val Val Arg Ala
        115                 120                 125

Cys Gly Cys His
    130

<210> SEQ ID NO 19
<211> LENGTH: 139
<212> TYPE: PRT
<213> ORGANISM: Artificial Sequence
<220> FEATURE:

-continued

<223> OTHER INFORMATION: BMP-7(OP-1)

<400> SEQUENCE: 19

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
        50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 20
<211> LENGTH: 139
<212> TYPE: PRT
<213> ORGANISM: Artificial Sequence
<220> FEATURE:
<223> OTHER INFORMATION: BMP-8(OP-2)

<400> SEQUENCE: 20

```
Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135
```

<210> SEQ ID NO 21
<211> LENGTH: 110
<212> TYPE: PRT
<213> ORGANISM: Artificial Sequence
<220> FEATURE:
<223> OTHER INFORMATION: BMP-9(GDF-2)

<400> SEQUENCE: 21

```
Ser Ala Gly Ala Gly Ser His Cys Gln Lys Thr Ser Leu Arg Val Asn
```

-continued

```
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
            35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
                100                 105                 110
```

<210> SEQ ID NO 22
<211> LENGTH: 108
<212> TYPE: PRT
<213> ORGANISM: Artificial Sequence
<220> FEATURE:
<223> OTHER INFORMATION: BMP-10

<400> SEQUENCE: 22

```
Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
            35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
                100                 105
```

<210> SEQ ID NO 23
<211> LENGTH: 125
<212> TYPE: PRT
<213> ORGANISM: Artificial Sequence
<220> FEATURE:
<223> OTHER INFORMATION: BMP-15 (GDF-9b)

<400> SEQUENCE: 23

```
Gln Ala Asp Gly Ile Ser Ala Glu Val Thr Ala Ser Ser Ser Lys His
1               5                   10                  15

Ser Gly Pro Glu Asn Asn Gln Cys Ser Leu His Pro Phe Gln Ile Ser
            20                  25                  30

Phe Arg Gln Leu Gly Trp Asp His Trp Ile Ile Ala Pro Pro Phe Tyr
            35                  40                  45

Thr Pro Asn Tyr Cys Lys Gly Thr Cys Leu Arg Val Leu Arg Asp Gly
    50                  55                  60

Leu Asn Ser Pro Asn His Ala Ile Ile Gln Asn Leu Ile Asn Gln Leu
65                  70                  75                  80

Val Asp Gln Ser Val Pro Arg Pro Ser Cys Val Pro Tyr Lys Tyr Val
                85                  90                  95
```

-continued

```
Pro Ile Ser Val Leu Met Ile Glu Ala Asn Gly Ser Ile Leu Tyr Lys
            100                 105                 110

Glu Tyr Glu Gly Met Ile Ala Glu Ser Cys Thr Cys Arg
        115                 120                 125

<210> SEQ ID NO 24
<211> LENGTH: 118
<212> TYPE: PRT
<213> ORGANISM: Artificial Sequence
<220> FEATURE:
<223> OTHER INFORMATION: GDF-1

<400> SEQUENCE: 24

Asp Ala Glu Pro Val Leu Gly Gly Gly Pro Gly Gly Ala Cys Arg Ala
1               5                   10                  15

Arg Arg Leu Tyr Val Ser Phe Arg Glu Val Gly Trp His Arg Trp Val
            20                  25                  30

Ile Ala Pro Arg Gly Phe Leu Ala Asn Tyr Cys Gln Gly Gln Cys Ala
        35                  40                  45

Leu Pro Val Ala Leu Ser Gly Ser Gly Gly Pro Pro Ala Leu Asn His
    50                  55                  60

Ala Val Leu Arg Ala Leu Met His Ala Ala Ala Pro Gly Ala Ala Asp
65                  70                  75                  80

Leu Pro Cys Cys Val Pro Ala Arg Leu Ser Pro Ile Ser Val Leu Phe
                85                  90                  95

Phe Asp Asn Ser Asp Asn Val Val Leu Arg Gln Tyr Glu Asp Met Val
            100                 105                 110

Val Asp Glu Cys Gly Cys
        115

<210> SEQ ID NO 25
<211> LENGTH: 114
<212> TYPE: PRT
<213> ORGANISM: Artificial Sequence
<220> FEATURE:
<223> OTHER INFORMATION: GDF-3(Vgr-2)

<400> SEQUENCE: 25

Ala Ala Ile Pro Val Pro Lys Leu Ser Cys Lys Asn Leu Cys His Arg
1               5                   10                  15

His Gln Leu Phe Ile Asn Phe Arg Asp Leu Gly Trp His Lys Trp Ile
            20                  25                  30

Ile Ala Pro Lys Gly Phe Met Ala Asn Tyr Cys His Gly Glu Cys Pro
        35                  40                  45

Phe Ser Leu Thr Ile Ser Leu Asn Ser Ser Asn Tyr Ala Phe Met Gln
    50                  55                  60

Ala Leu Met His Ala Val Asp Pro Glu Ile Pro Gln Ala Val Cys Ile
65                  70                  75                  80

Pro Thr Lys Leu Ser Pro Ile Ser Met Leu Tyr Gln Asp Asn Asn Asp
                85                  90                  95

Asn Val Ile Leu Arg His Tyr Glu Asp Met Val Val Asp Glu Cys Gly
            100                 105                 110

Cys Gly

<210> SEQ ID NO 26
<211> LENGTH: 120
<212> TYPE: PRT
<213> ORGANISM: Artificial Sequence
<220> FEATURE:
```

-continued

<223> OTHER INFORMATION: GDF-5(BMP-14)

<400> SEQUENCE: 26

```
Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
            35                  40                  45

Glu Gly Leu Cys Glu Phe Pro Leu Arg Ser His Leu Glu Pro Thr Asn
        50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
                100                 105                 110

Val Val Glu Ser Cys Gly Cys Arg
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: GDF-6(BMP-13)

<400> SEQUENCE: 27

```
Thr Ala Phe Ala Ser Arg His Gly Lys Arg His Gly Lys Lys Ser Arg
1               5                   10                  15

Leu Arg Cys Ser Lys Lys Pro Leu His Val Asn Phe Lys Glu Leu Gly
            20                  25                  30

Trp Asp Asp Trp Ile Ile Ala Pro Leu Glu Tyr Glu Ala Tyr His Cys
            35                  40                  45

Glu Gly Val Cys Asp Phe Pro Leu Arg Ser His Leu Glu Pro Thr Asn
        50                  55                  60

His Ala Ile Ile Gln Thr Leu Met Asn Ser Met Asp Pro Gly Ser Thr
65                  70                  75                  80

Pro Pro Ser Cys Cys Val Pro Thr Lys Leu Thr Pro Ile Ser Ile Leu
                85                  90                  95

Tyr Ile Asp Ala Gly Asn Asn Val Val Tyr Lys Gln Tyr Glu Asp Met
                100                 105                 110

Val Val Glu Ser Cys Gly Cys Arg
        115                 120
```

<210> SEQ ID NO 28
<211> LENGTH: 129
<212> TYPE: PRT
<213> ORGANISM: Artificial Sequence
<220> FEATURE:
<223> OTHER INFORMATION: GDF-7(BMP-12)

<400> SEQUENCE: 28

```
Thr Ala Leu Ala Gly Thr Arg Thr Ser Gln Gly Ser Gly Gly Gly Ala
1               5                   10                  15

Gly Arg Gly His Gly Arg Arg Gly Arg Ser Arg Cys Ser Arg Lys Pro
            20                  25                  30

Leu His Val Asp Phe Lys Glu Leu Gly Trp Asp Asp Trp Ile Ile Ala
```

-continued

```
        35              40              45

Pro Leu Asp Tyr Glu Ala Tyr His Cys Glu Gly Leu Cys Asp Phe Pro
    50              55              60

Leu Arg Ser His Leu Glu Pro Thr Asn His Ala Ile Ile Gln Thr Leu
65              70              75              80

Leu Asn Ser Met Ala Pro Asp Ala Ala Pro Ala Ser Cys Cys Val Pro
                85              90              95

Ala Arg Leu Ser Pro Ile Ser Ile Leu Tyr Ile Asp Ala Ala Asn Asn
            100             105             110

Val Val Tyr Lys Gln Tyr Glu Asp Met Val Val Glu Ala Cys Gly Cys
        115             120             125

Arg
```

```
<210> SEQ ID NO 29
<211> LENGTH: 109
<212> TYPE: PRT
<213> ORGANISM: Artificial Sequence
<220> FEATURE:
<223> OTHER INFORMATION: GDF-8(Myostatin)

<400> SEQUENCE: 29

Asp Phe Gly Leu Asp Cys Asp Glu His Ser Thr Glu Ser Arg Cys Cys
1               5               10              15

Arg Tyr Pro Leu Thr Val Asp Phe Glu Ala Phe Gly Trp Asp Trp Ile
            20              25              30

Ile Ala Pro Lys Arg Tyr Lys Ala Asn Tyr Cys Ser Gly Glu Cys Glu
        35              40              45

Phe Val Phe Leu Gln Lys Tyr Pro His Thr His Leu Val His Gln Ala
    50              55              60

Asn Pro Arg Gly Ser Ala Gly Pro Cys Cys Thr Pro Thr Lys Met Ser
65              70              75              80

Pro Ile Asn Met Leu Tyr Phe Asn Gly Lys Glu Gln Ile Ile Tyr Gly
                85              90              95

Lys Ile Pro Ala Met Val Val Asp Arg Cys Gly Cys Ser
            100             105
```

```
<210> SEQ ID NO 30
<211> LENGTH: 135
<212> TYPE: PRT
<213> ORGANISM: Artificial Sequence
<220> FEATURE:
<223> OTHER INFORMATION: GDF-9

<400> SEQUENCE: 30

Gly Gln Glu Thr Val Ser Ser Glu Leu Lys Lys Pro Leu Gly Pro Ala
1               5               10              15

Ser Phe Asn Leu Ser Glu Tyr Phe Arg Gln Phe Leu Leu Pro Gln Asn
            20              25              30

Glu Cys Glu Leu His Asp Phe Arg Leu Ser Phe Ser Gln Leu Lys Trp
            35              40              45

Asp Asn Trp Ile Val Ala Pro His Arg Tyr Asn Pro Arg Tyr Cys Lys
    50              55              60

Gly Asp Cys Pro Arg Ala Val Gly His Arg Tyr Gly Ser Pro Val His
65              70              75              80

Thr Met Val Gln Asn Ile Ile Tyr Glu Lys Leu Asp Ser Ser Val Pro
                85              90              95

Arg Pro Ser Cys Val Pro Ala Lys Tyr Ser Pro Leu Ser Val Leu Thr
```

-continued

```
                    100                 105                 110

Ile Glu Pro Asp Gly Ser Ile Ala Tyr Lys Glu Tyr Glu Asp Met Ile
        115                 120                 125

Ala Thr Lys Cys Thr Cys Arg
    130                 135

<210> SEQ ID NO 31
<211> LENGTH: 119
<212> TYPE: PRT
<213> ORGANISM: Artificial Sequence
<220> FEATURE:
<223> OTHER INFORMATION: GDF-10(BMP-3b)

<400> SEQUENCE: 31

Lys Thr Met Gln Lys Ala Arg Arg Lys Gln Trp Asp Glu Pro Arg Val
1               5                   10                  15

Cys Ser Arg Arg Tyr Leu Lys Val Asp Phe Ala Asp Ile Gly Trp Asn
            20                  25                  30

Glu Trp Ile Ile Ser Pro Lys Ser Phe Asp Ala Tyr Tyr Cys Ala Gly
        35                  40                  45

Ala Cys Glu Phe Pro Met Pro Lys Ile Val Arg Pro Ser Asn His Ala
    50                  55                  60

Thr Ile Gln Ser Ile Val Arg Ala Val Gly Ile Ile Pro Gly Ile Pro
65                  70                  75                  80

Glu Pro Cys Cys Val Pro Asp Lys Met Asn Ser Leu Gly Val Leu Phe
                85                  90                  95

Leu Asp Glu Asn Arg Asn Val Val Leu Lys Val Tyr Pro Asn Met Ser
            100                 105                 110

Val Asp Thr Cys Ala Cys Arg
        115

<210> SEQ ID NO 32
<211> LENGTH: 109
<212> TYPE: PRT
<213> ORGANISM: Artificial Sequence
<220> FEATURE:
<223> OTHER INFORMATION: GDF-11(BMP-11)

<400> SEQUENCE: 32

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 33
<211> LENGTH: 112
<212> TYPE: PRT
<213> ORGANISM: Artificial Sequence
<220> FEATURE:
```

<223> OTHER INFORMATION: GDF-15

<400> SEQUENCE: 33

```
Ala Arg Asn Gly Asp Asp Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Glu Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 34
<211> LENGTH: 110
<212> TYPE: PRT
<213> ORGANISM: Artificial Sequence
<220> FEATURE:
<223> OTHER INFORMATION: Nodal

<400> SEQUENCE: 34

```
His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
            20                  25                  30

Gln Tyr Asn Ala Tyr Arg Cys Glu Gly Glu Cys Pro Asn Pro Val Gly
            35                  40                  45

Glu Glu Phe His Pro Thr Asn His Ala Tyr Ile Gln Ser Leu Leu Lys
    50                  55                  60

Arg Tyr Gln Pro His Arg Val Pro Ser Thr Cys Cys Ala Pro Val Lys
65                  70                  75                  80

Thr Lys Pro Leu Ser Met Leu Tyr Val Asp Asn Gly Arg Val Leu Leu
                85                  90                  95

Asp His His Lys Asp Met Ile Val Glu Glu Cys Gly Cys Leu
            100                 105                 110
```

<210> SEQ ID NO 35
<211> LENGTH: 116
<212> TYPE: PRT
<213> ORGANISM: Artificial Sequence
<220> FEATURE:
<223> OTHER INFORMATION: Activin-bA

<400> SEQUENCE: 35

```
Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
            35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
```

-continued

```
65                  70              75                  80

Cys Val Pro Thr Lys Leu Arg Pro Met Ser Met Leu Tyr Tyr Asp Asp
                85                  90                  95

Gly Gln Asn Ile Ile Lys Lys Asp Ile Gln Asn Met Ile Val Glu Glu
                100                 105                 110

Cys Gly Cys Ser
        115

<210> SEQ ID NO 36
<211> LENGTH: 115
<212> TYPE: PRT
<213> ORGANISM: Artificial Sequence
<220> FEATURE:
<223> OTHER INFORMATION: Activin-bB

<400> SEQUENCE: 36

Gly Leu Glu Cys Asp Gly Arg Thr Asn Leu Cys Cys Arg Gln Gln Phe
1               5                   10                  15

Phe Ile Asp Phe Arg Leu Ile Gly Trp Asn Asp Trp Ile Ile Ala Pro
                20                  25                  30

Thr Gly Tyr Tyr Gly Asn Tyr Cys Glu Gly Ser Cys Pro Ala Tyr Leu
            35                  40                  45

Ala Gly Val Pro Gly Ser Ala Ser Ser Phe His Thr Ala Val Val Asn
        50                  55                  60

Gln Tyr Arg Met Arg Gly Leu Asn Pro Gly Thr Val Asn Ser Cys Cys
65                  70                  75                  80

Ile Pro Thr Lys Leu Ser Thr Met Ser Met Leu Tyr Phe Asp Asp Glu
                85                  90                  95

Tyr Asn Ile Val Lys Arg Asp Val Pro Asn Met Ile Val Glu Glu Cys
                100                 105                 110

Gly Cys Ala
        115

<210> SEQ ID NO 37
<211> LENGTH: 116
<212> TYPE: PRT
<213> ORGANISM: Artificial Sequence
<220> FEATURE:
<223> OTHER INFORMATION: Activin-bC

<400> SEQUENCE: 37

Gly Ile Asp Cys Gln Gly Gly Ser Arg Met Cys Cys Arg Gln Glu Phe
1               5                   10                  15

Phe Val Asp Phe Arg Glu Ile Gly Trp His Asp Trp Ile Ile Gln Pro
                20                  25                  30

Glu Gly Tyr Ala Met Asn Phe Cys Ile Gly Gln Cys Pro Leu His Ile
            35                  40                  45

Ala Gly Met Pro Gly Ile Ala Ala Ser Phe His Thr Ala Val Leu Asn
        50                  55                  60

Leu Leu Lys Ala Asn Thr Ala Ala Gly Thr Thr Gly Gly Gly Ser Cys
65                  70                  75                  80

Cys Val Pro Thr Ala Arg Arg Pro Leu Ser Leu Leu Tyr Tyr Asp Arg
                85                  90                  95

Asp Ser Asn Ile Val Lys Thr Asp Ile Pro Asp Met Val Val Glu Ala
                100                 105                 110

Cys Gly Cys Ser
        115
```

-continued

```
<210> SEQ ID NO 38
<211> LENGTH: 114
<212> TYPE: PRT
<213> ORGANISM: Artificial Sequence
<220> FEATURE:
<223> OTHER INFORMATION: Activin-bE

<400> SEQUENCE: 38

Thr Pro Thr Cys Glu Pro Ala Thr Pro Leu Cys Cys Arg Arg Asp His
1               5                   10                  15

Tyr Val Asp Phe Gln Glu Leu Gly Trp Arg Asp Trp Ile Leu Gln Pro
                20                  25                  30

Glu Gly Tyr Gln Leu Asn Tyr Cys Ser Gly Gln Cys Pro Pro His Leu
            35                  40                  45

Ala Gly Ser Pro Gly Ile Ala Ala Ser Phe His Ser Ala Val Phe Ser
        50                  55                  60

Leu Leu Lys Ala Asn Asn Pro Trp Pro Ala Ser Thr Ser Cys Cys Val
65                  70                  75                  80

Pro Thr Ala Arg Arg Pro Leu Ser Leu Leu Tyr Leu Asp His Asn Gly
                85                  90                  95

Asn Val Val Lys Thr Asp Val Pro Asp Met Val Val Glu Ala Cys Gly
            100                 105                 110

Cys Ser

<210> SEQ ID NO 39
<211> LENGTH: 134
<212> TYPE: PRT
<213> ORGANISM: Artificial Sequence
<220> FEATURE:
<223> OTHER INFORMATION: Inhibin-a

<400> SEQUENCE: 39

Ser Thr Pro Leu Met Ser Trp Pro Trp Ser Pro Ser Ala Leu Arg Leu
1               5                   10                  15

Leu Gln Arg Pro Pro Glu Glu Pro Ala Ala His Ala Asn Cys His Arg
                20                  25                  30

Val Ala Leu Asn Ile Ser Phe Gln Glu Leu Gly Trp Glu Arg Trp Ile
            35                  40                  45

Val Tyr Pro Pro Ser Phe Ile Phe His Tyr Cys His Gly Gly Cys Gly
        50                  55                  60

Leu His Ile Pro Pro Asn Leu Ser Leu Pro Val Pro Gly Ala Pro Pro
65                  70                  75                  80

Thr Pro Ala Gln Pro Tyr Ser Leu Leu Pro Gly Ala Gln Pro Cys Cys
                85                  90                  95

Ala Ala Leu Pro Gly Thr Met Arg Pro Leu His Val Arg Thr Thr Ser
            100                 105                 110

Asp Gly Gly Tyr Ser Phe Lys Tyr Glu Thr Val Pro Asn Leu Leu Thr
        115                 120                 125

Gln His Cys Ala Cys Ile
    130

<210> SEQ ID NO 40
<211> LENGTH: 112
<212> TYPE: PRT
<213> ORGANISM: Artificial Sequence
<220> FEATURE:
<223> OTHER INFORMATION: TGF-b1

<400> SEQUENCE: 40
```

-continued

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 41
<211> LENGTH: 112
<212> TYPE: PRT
<213> ORGANISM: Artificial Sequence
<220> FEATURE:
<223> OTHER INFORMATION: TGF-b2

<400> SEQUENCE: 41

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 42
<211> LENGTH: 112
<212> TYPE: PRT
<213> ORGANISM: Artificial Sequence
<220> FEATURE:
<223> OTHER INFORMATION: TGF-b3

<400> SEQUENCE: 42

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
```

```
                 85                  90                  95
Lys Val Glu Gln Leu Ser Asn Met Val Val Lys Ser Cys Lys Cys Ser
             100                 105                 110
```

```
<210> SEQ ID NO 43
<211> LENGTH: 6
<212> TYPE: PRT
<213> ORGANISM: Artificial Sequence
<220> FEATURE:
<223> OTHER INFORMATION: derived from Activin A

<400> SEQUENCE: 43

Ile Ile Lys Lys Asp Ile
1               5
```

```
<210> SEQ ID NO 44
<211> LENGTH: 6
<212> TYPE: PRT
<213> ORGANISM: Artificial Sequence
<220> FEATURE:
<223> OTHER INFORMATION: derived from BMP 2

<400> SEQUENCE: 44

Val Val Leu Lys Lys Tyr
1               5
```

```
<210> SEQ ID NO 45
<211> LENGTH: 6
<212> TYPE: PRT
<213> ORGANISM: Artificial Sequence
<220> FEATURE:
<223> OTHER INFORMATION: derived from AB204

<400> SEQUENCE: 45

Val Ile Leu Lys Lys Tyr
1               5
```

```
<210> SEQ ID NO 46
<211> LENGTH: 30
<212> TYPE: PRT
<213> ORGANISM: Artificial Sequence
<220> FEATURE:
<223> OTHER INFORMATION: derived from BMP2

<400> SEQUENCE: 46

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp
            20                  25                  30
```

```
<210> SEQ ID NO 47
<211> LENGTH: 18
<212> TYPE: PRT
<213> ORGANISM: Artificial Sequence
<220> FEATURE:
<223> OTHER INFORMATION: derived from BMP2

<400> SEQUENCE: 47

Trp Ile Val Ala Pro Pro Gly Tyr His Ala Phe Tyr Cys His Gly Glu
1               5                   10                  15

Cys Pro
```

```
<210> SEQ ID NO 48
<211> LENGTH: 20
<212> TYPE: PRT
```

-continued

<213> ORGANISM: Artificial Sequence
<220> FEATURE:
<223> OTHER INFORMATION: derived from BMP2

<400> SEQUENCE: 48

Phe Pro Leu Ala Asp His Leu Asn Ser Thr Asn His Ala Ile Val Gln
1               5                   10                  15

Thr Leu Val Asn
            20

<210> SEQ ID NO 49
<211> LENGTH: 13
<212> TYPE: PRT
<213> ORGANISM: Artificial Sequence
<220> FEATURE:
<223> OTHER INFORMATION: derived from BMP2

<400> SEQUENCE: 49

Ser Val Asn Ser Lys Ile Pro Lys Ala Cys Cys Val Pro
1               5                   10

<210> SEQ ID NO 50
<211> LENGTH: 12
<212> TYPE: PRT
<213> ORGANISM: Artificial Sequence
<220> FEATURE:
<223> OTHER INFORMATION: derived from BMP2

<400> SEQUENCE: 50

Thr Glu Leu Ser Ala Ile Ser Met Leu Tyr Tyr Asp
1               5                   10

<210> SEQ ID NO 51
<211> LENGTH: 21
<212> TYPE: PRT
<213> ORGANISM: Artificial Sequence
<220> FEATURE:
<223> OTHER INFORMATION: derived from BMP2

<400> SEQUENCE: 51

Glu Asn Glu Lys Val Val Leu Lys Asn Tyr Gln Asp Met Val Val Glu
1               5                   10                  15

Gly Cys Gly Cys Arg
            20

<210> SEQ ID NO 52
<211> LENGTH: 29
<212> TYPE: PRT
<213> ORGANISM: Artificial Sequence
<220> FEATURE:
<223> OTHER INFORMATION: derived from Activin-betaA

<400> SEQUENCE: 52

Arg Gly Leu Glu Cys Asp Gly Lys Val Asn Ile Cys Cys Lys Lys Gln
1               5                   10                  15

Phe Phe Val Ser Phe Lys Asp Ile Gly Trp Asn Asp Trp
            20                  25

<210> SEQ ID NO 53
<211> LENGTH: 18
<212> TYPE: PRT
<213> ORGANISM: Artificial Sequence
<220> FEATURE:
<223> OTHER INFORMATION: derived from Activin-betaA

<400> SEQUENCE: 53

```
Trp Ile Ile Ala Pro Ser Gly Tyr His Ala Asn Tyr Cys Glu Gly Glu
1               5                   10                  15

Cys Pro

<210> SEQ ID NO 54
<211> LENGTH: 19
<212> TYPE: PRT
<213> ORGANISM: Artificial Sequence
<220> FEATURE:
<223> OTHER INFORMATION: derived from Activin-betaA

<400> SEQUENCE: 54

Ser His Ile Ala Gly Thr Ser Gly Ser Ser Leu Ser Phe His Ser Thr
1               5                   10                  15

Leu Val Asn

<210> SEQ ID NO 55
<211> LENGTH: 19
<212> TYPE: PRT
<213> ORGANISM: Artificial Sequence
<220> FEATURE:
<223> OTHER INFORMATION: derived from Activin-betaA

<400> SEQUENCE: 55

His Tyr Arg Met Arg Gly His Ser Pro Phe Ala Asn Leu Lys Ser Cys
1               5                   10                  15

Cys Val Pro

<210> SEQ ID NO 56
<211> LENGTH: 12
<212> TYPE: PRT
<213> ORGANISM: Artificial Sequence
<220> FEATURE:
<223> OTHER INFORMATION: derived from Activin-betaA

<400> SEQUENCE: 56

Thr Lys Leu Arg Pro Met Ser Met Leu Tyr Tyr Asp
1               5                   10

<210> SEQ ID NO 57
<211> LENGTH: 21
<212> TYPE: PRT
<213> ORGANISM: Artificial Sequence
<220> FEATURE:
<223> OTHER INFORMATION: derived from Activin-betaA

<400> SEQUENCE: 57

Asp Gly Gln Asn Ile Ile Lys Lys Asp Ile Gln Asn Met Ile Val Glu
1               5                   10                  15

Glu Cys Gly Cys Ser
            20

<210> SEQ ID NO 58
<211> LENGTH: 55
<212> TYPE: PRT
<213> ORGANISM: Artificial Sequence
<220> FEATURE:
<223> OTHER INFORMATION: derived from BMP7

<400> SEQUENCE: 58

Met Ser Thr Gly Ser Lys Gln Arg Ser Gln Asn Arg Ser Lys Thr Pro
1               5                   10                  15

Lys Asn Gln Glu Ala Leu Arg Met Ala Asn Val Ala Glu Asn Ser Ser
```

```
                20              25              30
Ser Asp Gln Arg Gln Ala Cys Lys Lys His Glu Leu Tyr Val Ser Phe
         35              40              45
Arg Asp Leu Gly Trp Gln Asp
    50              55

<210> SEQ ID NO 59
<211> LENGTH: 18
<212> TYPE: PRT
<213> ORGANISM: Artificial Sequence
<220> FEATURE:
<223> OTHER INFORMATION: derived from BMP7

<400> SEQUENCE: 59

Trp Ile Ile Ala Pro Glu Gly Tyr Ala Ala Tyr Tyr Cys Glu Gly Glu
1               5               10              15

Cys Ala

<210> SEQ ID NO 60
<211> LENGTH: 20
<212> TYPE: PRT
<213> ORGANISM: Artificial Sequence
<220> FEATURE:
<223> OTHER INFORMATION: derived from BMP7

<400> SEQUENCE: 60

Gly Pro Leu Asn Ser Tyr Met Asn Ala Thr Asn His Ala Ile Val Gln
1               5               10              15

Thr Leu Val His
            20

<210> SEQ ID NO 61
<211> LENGTH: 14
<212> TYPE: PRT
<213> ORGANISM: Artificial Sequence
<220> FEATURE:
<223> OTHER INFORMATION: derived from BMP7

<400> SEQUENCE: 61

Phe Ile Asn Pro Glu Thr Val Pro Lys Pro Cys Cys Ala Pro
1               5               10

<210> SEQ ID NO 62
<211> LENGTH: 12
<212> TYPE: PRT
<213> ORGANISM: Artificial Sequence
<220> FEATURE:
<223> OTHER INFORMATION: derived from BMP7

<400> SEQUENCE: 62

Thr Gln Leu Asn Ala Ile Ser Val Leu Tyr Phe Asp
1               5               10

<210> SEQ ID NO 63
<211> LENGTH: 21
<212> TYPE: PRT
<213> ORGANISM: Artificial Sequence
<220> FEATURE:
<223> OTHER INFORMATION: derived from BMP7

<400> SEQUENCE: 63

Asp Ser Ser Asn Val Ile Leu Lys Lys Tyr Arg Asn Met Val Val Arg
1               5               10              15

Ala Cys Gly Cys His
```

-continued

```
          20

<210> SEQ ID NO 64
<211> LENGTH: 32
<212> TYPE: PRT
<213> ORGANISM: Artificial Sequence
<220> FEATURE:
<223> OTHER INFORMATION: derived from BMP2

<400> SEQUENCE: 64

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Ile Ile
            20                  25                  30
```